US006043077A

United States Patent [19]
Barber et al.

[11] Patent Number: 6,043,077
[45] Date of Patent: Mar. 28, 2000

[54] HEPATITIS C VIRUS RIBOZYMES

[75] Inventors: Jack R. Barber; Peter J. Welch; Richard Tritz, all of San Diego; SoonPin Yei, Carlsbad; Mang Yu, San Diego, all of Calif.

[73] Assignee: Immusol Inc., San Diego, Calif.

[21] Appl. No.: 08/954,210

[22] Filed: Oct. 20, 1997

Related U.S. Application Data

[63] Continuation-in-part of application No. 08/608,862, filed as application No. PCT/US97/03304, Feb. 27, 1997, abandoned.

[51] Int. Cl.⁷ .......................... C07H 21/04; C12N 15/85; C12N 15/63
[52] U.S. Cl. .......................... 435/236; 435/6; 435/91.31; 435/320.1; 435/325; 435/366; 435/363; 435/375; 536/23.1; 536/23.2; 536/24.1; 536/24.5
[58] Field of Search .................. 435/6, 91.31, 320.1, 435/325, 366, 363, 375; 536/23.1, 23.2, 24.1, 24.5; 514/44

[56] References Cited

U.S. PATENT DOCUMENTS

| | | | |
|---|---|---|---|
| 5,254,678 | 10/1993 | Haseloff et al. | 536/23.2 |
| 5,527,895 | 6/1996 | Hampel et al. | 536/23.2 |
| 5,610,054 | 3/1997 | Draper | 435/363 |

FOREIGN PATENT DOCUMENTS

| | | |
|---|---|---|
| 558 944 A2 | 9/1993 | European Pat. Off. . |
| WO 93/23569 | 11/1993 | WIPO . |
| WO 94/02595 | 2/1994 | WIPO . |
| WO 95/19429 | 7/1995 | WIPO . |
| WO 95/29241 | 11/1995 | WIPO . |
| WO 96/18419 | 6/1996 | WIPO . |

OTHER PUBLICATIONS

Sakamoto et al., "Inhibition Of Hepatitis C Virus–Directed Translation By Hammered Ribozymes In–Vitro," *Hepatology* 22(4, Part 2):p. 330A, Abstract No. 896, 1995.
Stull and Szoka, Jr., "Antigene, Ribozyme and Aptamer Nucleic Acid Drugs: Progress and Prospects," *Pharmaceutical Research* 12(4):465–483, 1995.
Welch et al., "A potential therapeutic application of hairpin ribozymes: in vitro and in vivo studies of gene therapy for hepatitis C virus infection," *Gene Therapy* 3:994–1001, 1996.
Anderson et al., "Mutagenesis of the hairpin ribozyme," *Nucleic Acids Research* 22(6):1096–1100, 1994.
Bhandari and Wright, "Hepatitis C: An Overview," *Annu. Rev. Med.* 46:309–317, 1995.
Blum, Hubert E., "Variants of Hepatitis B, C and D Viruses: Molecular Biology and Clinical Significance," *Digestion* 56:85–95, 1995.

Carreño and Quiroga, "Biologic response modifiers in chronic hepatitis C," *Journal of Hepatology* 22(Suppl. 1):122–126, 1995.
Davis et al., "Therapy For Chronic Hepatitis C," *Viral Hepatitis* 23(3):603–613, 1994.
Fried and Hoofnagle, "Therapy of Hepatitis C," *Seminars in Liver Disease* 15(1):82–91, 1995.
Gitnick, G., "Hepatitis C in 1994," *Scan J. Gastroenterol* 30(Suppl. 208):147–8, 1995.
Hirschman, Shalom Z., "Current Therapeutic Approaches to Viral Hepatitis," *Clinical Infectious Diseases* 20:741–6, 1995.
Iwarson et al., "Hepatitis C: Natural History of a Unique Infection," *Clinical Infectious Diseases* 20:1361–70, 1995.
Marcellin et al., "Hepatitis C virus infection, alpha interferon therapy and thyroid dysfunction," *Journal of Hepatology* 22:364–369, 1995.
Nagayama et al., "Exacerbation of Thyroid Autoimmunity by Interferon α Treatment in Patients with Chronic Viral Hepatitis: Our Studies and Review of the Literature," *Endocrine Journal* 41(5):565–572, 1994.
Nesbitt and Goodchild, "Further Studies on the Use of Oligonucleotides Facilitators to Increase Ribozyme Turnover," *Antisene Research and Development* 4:243–249, 1994.
Olynyk and Bacon, "Hepatitis C. Recent advances in understanding and management," *Postgraduate Medicine* 98(1):79–81, 86–87, 91–92, 94, 1995.
Ramos–Soriano and Schwartz, "Recent Advances In The Hepatitides," *Pediatric Gastroenterology, Part I* 23(4):753–767, 1994.
Rubin et al., "Chronic Hepatitis C. Advances in Diagnostic Testing and Therapy," *Arch Intern Med.* 154:387–392, 1994.
Scotiniotis et al., "Hepatitis C: Diagnosis and Treatment," *JGIM* 10:273–282, 1995.
Trépo et al., "Interferon therapy for hepatitis C," *Antiviral Research* 24:155–163, 1994.
Wong and Heathcote, "The Role Of Interferon In The Treatment Of Viral Hepatitis," *Pharmac. Ther.* 63:177–186, 1994.
Stull et al. Antigene, Ribozyme and Aptamer Nucleic Acid Drugs: Progress and Prospects. Pharmaceutical Research vol. 12(4): 465–483, 1995.
Branch A. A Good Antisense Molecule is Hard to Find. TIBS vol. 23:45–50, Feb. 1998.

*Primary Examiner*—John S. Brusca
*Assistant Examiner*—Sean McGarry
*Attorney, Agent, or Firm*—Seed and Berry LLP

[57] ABSTRACT

This invention provides ribozymes useful to treat or prevent Hepatitis C Virus ("HCV") infection or disease in an organism or subject, as well as methods of treating an HCV infection or disease. Reagents such as vectors, host cells, DNA molecules coding for these ribozymes useful in methods of treatment and prevention of HCV infection or disease are also provided.

29 Claims, 31 Drawing Sheets

HCV expression:

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (xi) SEQUENCE DESCRIPTION: SEQ ID NO:1:

NNNBNGUCNN NNNN                         14

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:2:

NNNBNGUCNN NNNNN                       15

(2) INFORMATION FOR SEQ ID NO:3:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:3:

NNNBNGUCNN NNNNNN                      16

(2) INFORMATION FOR SEQ ID NO:4:

(i) SEQUENCE CHARACTERISTICS:
      (A) LENGTH: 17 base pairs (B) TYPE: nucleic acid
        (C) STRANDEDNESS: single
        (D) TOPOLOGY: linear (xi) SEQUENCE DESCRIPTION: SEQ ID NO:4:

NNNBNGUCNN NNNNNNN                                                  17

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

NNNBNGUCNN NNNNNNNN                                                 18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

GCCAGCCCCC TGATGGGG                                                 18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

CACCTGATAA GCGGAAGC                                                 18

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:8:

ACCGGGUCCU UUCUUG                                                   16

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:9:

UAGUGGUCUG CGGAAC                                                   16

(2) INFORMATION FOR SEQ ID NO:10:

(i) SEQUENCE CHARACTERISTICS:
        (A) LENGTH: 16 base pairs
        (B) TYPE: nucleic acid (C) STRANDEDNESS: single
            (D) TOPOLOGY: linear (xi) SEQUENCE DESCRIPTION: SEQ ID NO:10:

CGGUGGUCAG AUCGUU                                                          16

(2) INFORMATION FOR SEQ ID NO:11:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:11:

GAGCGGUCGC AACCUC                                                          16

(2) INFORMATION FOR SEQ ID NO:12:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:12:

GAGCGGUCGC AACCU                                                           15

(2) INFORMATION FOR SEQ ID NO:13:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:13:

GAGCGGUCGC AACC                                                            14

(2) INFORMATION FOR SEQ ID NO:14:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:14:

CUCCUGUCAC CCCGCG                                                          16

(2) INFORMATION FOR SEQ ID NO:15:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:15:

CUACUGUCUU CACGCA                                                          16

(2) INFORMATION FOR SEQ ID NO:16:

(i) SEQUENCE CHARACTERISTICS:
            (A) LENGTH: 16 base pairs
            (B) TYPE: nucleic acid
            (C) STRANDEDNESS: single (D) TOPOLOGY: linear (xi) SEQUENCE DESCRIPTION: SEQ ID NO:16:

AAAGCGUCUA GCCAUG                                                              16

(2) INFORMATION FOR SEQ ID NO:17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:17:

UGAGUGUCGU GCAGCC                                                              16

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:18:

GUUGGGUCGC GAAAGG                                                              16

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:19:

CGCUCGUCGG CGCCCC                                                              16

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:20:

AACUGGUCGC CUACAA                                                              16

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:21:

AUAGGGUCAG CGGUUG                                                              16

(2) INFORMATION FOR SEQ ID NO:22:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:22:

ACCUUGUCAC CACACU                                                    16

(2) INFORMATION FOR SEQ ID NO:23:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:23:

AUGCGGUCCC CGGUCU                                                    16

(2) INFORMATION FOR SEQ ID NO:24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:24:

CCCCGGUCUU CACGGA                                                    16

(2) INFORMATION FOR SEQ ID NO:25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:25:

GACGUGUCCG UCAUAC                                                    16

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:26:

CAUGUGUCAC CCAGAC                                                    16

(2) INFORMATION FOR SEQ ID NO:27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:27:

AGACAGUCGA UUUCAG                                                    16

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:28:

GCGGUGUCGC GCUCAC                                                          16

(2) INFORMATION FOR SEQ ID NO:29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:29:

AGGUCGUCAC UAGCAC                                                          16

(2) INFORMATION FOR SEQ ID NO:30:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:30:

CUCCAGUCCA AGCUCC                                                          16

(2) INFORMATION FOR SEQ ID NO:31:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:31:

GUUGAGUCGU ACUCCU                                                          16

(2) INFORMATION FOR SEQ ID NO:32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:32:

UCUUGGUCUA CCGUGA                                                          16

(2) INFORMATION FOR SEQ ID NO:33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:33:

ACAUGGUCUA UGCCAC                                                          16

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:34:

AAGGCGUCCA CAGUUA 16

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:35:

ACGUGGUCUC CACCCU 16

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:36:

GGCCUGUCGA GCUGCA 16

(2) INFORMATION FOR SEQ ID NO:37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:37:

CUACUGUCCC AAGGGG 16

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:38:

GGAGUGUCGC CCCCAA 16

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:39:

GGGGGGUCCU GGAGGC 16

(2) INFORMATION FOR SEQ ID NO:40:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:40:

CGGUCGUCCU GGCAAU 16

(2) INFORMATION FOR SEQ ID NO:41:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:41:

ACCCGGUCGU CCAGGC 16

(2) INFORMATION FOR SEQ ID NO:42:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:42:

UAGCAGUCUC GCGGGG 16

(2) INFORMATION FOR SEQ ID NO:43:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:43:

GCACGGUCUA CGAGAC 16

(2) INFORMATION FOR SEQ ID NO:44:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:44:

CGGGGGUCCG UGGGGC 16

(2) INFORMATION FOR SEQ ID NO:45:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:45:

ACGCCGUCCU CCAGAA 16

(2) INFORMATION FOR SEQ ID NO:46:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (xi) SEQUENCE DESCRIPTION: SEQ ID NO:46:

GAGCAGUCAU UCGUGA 16

(2) INFORMATION FOR SEQ ID NO:47:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:47:

GCGGUGUCCG CCCCCC                                                16

(2) INFORMATION FOR SEQ ID NO:48:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:48:

GUCGAGUCAG UUGAGU                                                16

(2) INFORMATION FOR SEQ ID NO:49:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:49:

CAGCCGUCUC CGCUUG                                                16

(2) INFORMATION FOR SEQ ID NO:50:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:50:

AGAGCGUCUG UUGCCA                                                16

(2) INFORMATION FOR SEQ ID NO:51:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:51:

UUGCAGUCGA UCACCG                                                16

(2) INFORMATION FOR SEQ ID NO:52:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:52:

CCCGCGUCAU AGCACU                                                16

(2) INFORMATION FOR SEQ ID NO:53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:53:

GAGCAGUCCU CAUUAA                                                        16

(2) INFORMATION FOR SEQ ID NO:54:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:54:

UACCCGUCAC GUAGUG                                                        16

(2) INFORMATION FOR SEQ ID NO:55:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:55:

ACGUUGUCGG UGGUCA                                                        16

(2) INFORMATION FOR SEQ ID NO:56:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:56:

CAACCGUCCU CUUUUU                                                        16

(2) INFORMATION FOR SEQ ID NO:57:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:57:

UCAGGGUCCC CCGGCU                                                        16

(2) INFORMATION FOR SEQ ID NO:58:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:58:

GACCCGUCGC UGAGAU                                                        16

(2) INFORMATION FOR SEQ ID NO:59:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:59:

AGUCUGUCAA AGGUGA                                    16

(2) INFORMATION FOR SEQ ID NO:60:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:60:

GGGGCGUCAG CUUGCA                                    16

(2) INFORMATION FOR SEQ ID NO:61:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:61:

GUUGAGUCAA AGCAGC                                    16

(2) INFORMATION FOR SEQ ID NO:62:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:62:

AAUUAGUCAG GGGGCC                                    16

(2) INFORMATION FOR SEQ ID NO:63:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:63:

UAGUCGUCAG CACGCC                                    16

(2) INFORMATION FOR SEQ ID NO:64:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:64:

GUGCAGUCCU GGAGCU                                    16

(2) INFORMATION FOR SEQ ID NO:65:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (xi) SEQUENCE DESCRIPTION: SEQ ID NO:65:

ACCUAGUCAU AGCCUC                                                           16

(2) INFORMATION FOR SEQ ID NO:66:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (xi) SEQUENCE DESCRIPTION: SEQ ID NO:66:

AGUGUGUCUA GGUCUC                                                           16

(2) INFORMATION FOR SEQ ID NO:67:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (xi) SEQUENCE DESCRIPTION: SEQ ID NO:67:

GCGGGGUCGG GCACGA                                                           16

(2) INFORMATION FOR SEQ ID NO:68:

(i) SEQUENCE CHARACTERISTICS:
              (A) LENGTH: 41 base pairs
              (B) TYPE: nucleic acid
              (C) STRANDEDNESS: single
              (D) TOPOLOGY: linear (xi) SEQUENCE DESCRIPTION: SEQ ID NO:68:

GCGGATCCGG AGGTTGCAGA AGCTCACCAG AGAAACACAC G                                41

(2) INFORMATION FOR SEQ ID NO:69:

(i) SEQUENCE CHARACTERISTICS:
              (A) LENGTH: 44 base pairs
              (B) TYPE: nucleic acid
              (C) STRANDEDNESS: single
              (D) TOPOLOGY: linear (xi) SEQUENCE DESCRIPTION: SEQ ID NO:69:

GGGACGCGTA CCAGGTAATA TACCACAACG TGTGTTTCTC TGGT                             44

(2) INFORMATION FOR SEQ ID NO:70:

(i) SEQUENCE CHARACTERISTICS:
              (A) LENGTH: 53 base pairs
              (B) TYPE: nucleic acid
              (C) STRANDEDNESS: single
              (D) TOPOLOGY: linear (xi) SEQUENCE DESCRIPTION: SEQ ID NO:70:

GGAGGUUGCA GAAGCUCACC AGAGAAACAC ACGUUGUGGU AUAUUACCUG GUA                   53

(2) INFORMATION FOR SEQ ID NO:71:

```
        (i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:71:

GAGCGGUCGC AACCUCC                                                  17

(2) INFORMATION FOR SEQ ID NO:72:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (xi) SEQUENCE DESCRIPTION: SEQ ID NO:72:

GGGACGCGTA CCAGGTAATA TACCACGGAC CGAAGTCCGT GTGTTTCTCT GGT           53

(2) INFORMATION FOR SEQ ID NO:73:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (xi) SEQUENCE DESCRIPTION: SEQ ID NO:73:

GGAGGUUGCA GAAGCUCACC AGAGAAACAC ACGGACUUCG GUCCGUGGUA UAUUACCUGG    60

UA                                                                  62
```

HEPATITIS C VIRUS RIBOZYMES

CROSS-REFERENCE TO RELATED APPLICATION

This application is a continuation-in-part of U.S. application Ser. No. 08/608,862, filed Feb. 29, 1996 now abandoned; and claims priority under 35 U.S.C. §§ 119/365 from pending PCT Application No. PCT/US97/03304, filed Feb. 27, 1997, which applications are incorporated by reference in their entirety.

TECHNICAL FIELD

The present invention relates generally to ribozymes, and more specifically, to ribozymes which are capable of cleaving Hepatitis C Virus nucleic acids, as well as to methods which utilize such ribozymes.

BACKGROUND OF THE INVENTION

Hepatitis C Virus ("HCV") is an RNA virus which is responsible for approximately 75% of all cases of non-A, non-B hepatitis. Based upon epidemiologic and serologic surveys, it has been estimated that at least 1% to 2% of the world population is chronically infected with HCV (Davis et al., "Therapy for Chronic Hepatitis C" in Gastroenterology Clinics of North America, pp. 603–613, 1995). In the United States, approximately 150,000 acute cases occur annually, where it is the ninth leading cause of death. Moreover, approximately 50% of the acutely infected individuals go on to develop chronic liver disease, and of these, 25% will develop cirrhosis. In addition, on a worldwide basis, 50% of the cases of hepatocellular carcinoma are correlated with HCV infection.

HCV is a positive-stranded RNA virus that is related to the flaviviridae family. The virus, which was isolated and characterized in 1989 (Choo et al., *Science* 244:362–364, 1989) has an ~9.5 Kb linear genome that replicates through a double stranded RNA intermediate, mediated by a virally encoded RNA-dependent RNA polymerase. There is no known DNA intermediate in the replication process. Presumably, because its replication is exclusively through RNA polymerases, which lack proofreading activities, variability in the coding sequences is a hallmark of individual HCV isolates.

At present, the only therapy which shows some promise for the treatment acute and chronic cases of HCV is alpha interferon (Fried and Hoofnagle, *Seminars in Liver Disease* 15(1):82–91, 1995). Treatment with alpha interferon however, particularly for chronic patients, produces only temporary results. In particular, in most studies where patients with chronic HCV infections are treated with alpha interferon, only 20% to 25% maintain a sustained, long-term response (Fried and Hoofnagle, supra). In addition, treatment with alpha interferon can produce a wide array of side effects, including systemic effects (e.g., fatigue, fever, headache, anorexia, weight loss, nausea, vomiting, diarrhea, and hair loss), neurologic and psychological effects, an increased susceptibility to infections, as well as an assortment of autoimmune diseases.

The present invention provides an effective treatment to combat HCV infection, and further provides other, related advantages.

SUMMARY OF THE INVENTION

The present invention provides ribozymes useful to treat or prevent Hepatitis C Virus ("HCV") infection or disease in an organism or subject, as well as methods of treating HCV infection or disease. Reagents such as vectors, host cells, DNA molecules coding for these ribozymes useful in methods of treatment and prevention of HCV infection or disease also are provided.

Accordingly, in one aspect the present invention ribozymes are provided which have the ability to inhibit replication, infectivity, or gene expression of a hepatitis C virus. Within certain embodiments, the ribozyme is a hammerhead or hairpin ribozyme. Within other embodiments, the ribozyme cleaves genomic strand RNA (either the positive or negative strand), representative examples of which include the sequences set forth in Table I, below. In other aspects, the present invention also provides nucleic acid molecules encoding such ribozymes where, within certain embodiments the nucleic acid molecule is DNA or cDNA. Within preferred embodiments, the nucleic acid molecule is under the control of a promoter to transcribe the nucleic acid molecule.

In another aspect, the present invention provides host cells containing the ribozymes described herein, vectors comprising a promoter operatively linked to the nucleic acid molecule which encodes the ribozymes described herein, and host cells containing such vectors. Within certain embodiments, the vector is a plasmid, a viral vector, retrotransposon, or a cosmid. Representative examples of promoters include the polIII and CMV promoters.

In a further aspect, the present invention provides methods for producing a ribozyme, the ribozyme being able to inhibit hepatitis C viral infection and replication in a cell, comprising the step of providing a nucleic acid molecule (e.g., DNA) encoding a ribozyme under the transcriptional control of a promoter (e.g., in a vector), and transcribing the nucleic acid molecule to produce the ribozyme. The method may also further comprise purifying the ribozyme so produced. The ribozyme may be produced in vitro, in vivo or ex vivo.

In yet another aspect, the present invention provides methods of interfering with or preventing HCV replication in a cell infected with HCV, comprising the step of introducing into a cell an effective amount of the ribozymes described herein. In one embodiment, such methods comprise introducing into the cell an effective amount of DNA encoding a ribozyme as described herein and transcribing the DNA to produce the ribozyme.

In still a further aspect, the present invention provides methods of preventing hepatitis C viral infection in a cell susceptible to infection with HCV, comprising the step of introducing into the cell an effective amount of a nucleic acid molecule (e.g., DNA) encoding a ribozyme as described herein and transcribing the DNA to produce the ribozyme.

In preferred embodiments, the methods further comprise administering the cell transduced with a retroviral vector to a mammal of the same species as that from which the transduced cell was obtained. In other preferred embodiments, the cell transduced with the retroviral vector has been obtained from the mammal receiving the transduced cell.

The above-described methods, as well as the compositions described herein, may be utilized to treat or prevent HCV infection or disease in a wide variety of warm-blooded animals or mammals, including for example, humans.

These and other aspects of the present invention will become evident upon reference to the following detailed description and attached drawings. In addition, various references are set forth herein that describe in more detail certain procedures or compositions (e.g., plasmids, etc.), and are therefore incorporated by reference in their entirety as if each were individually noted for incorporation.

DETAILED DESCRIPTION OF THE INVENTION

Definitions

Figure 1:
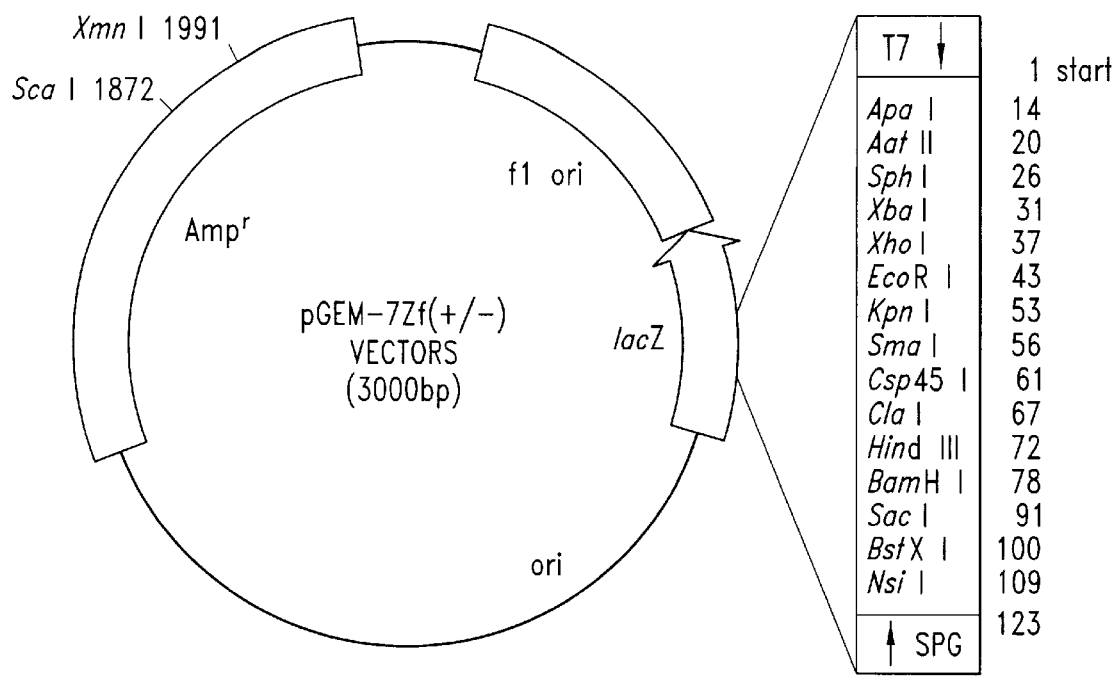
FIG. 1 is a schematic illustration of vector pGem7Z (Promega, Madison, Wis.).

Prior to setting forth the invention, it may be helpful to an understanding thereof to first set forth definitions of certain terms that will be used hereinafter.

"Ribozyme" refers to a nucleic acid molecule which is capable of cleaving a specific nucleic acid sequence. Ribozymes may be composed of RNA, DNA, nucleic acid analogues (e.g., phosphorothioates), or any combination of these (e.g., DNA/RNA chimerics). Within particularly preferred embodiments, a ribozyme should be understood to refer to RNA molecules that contain anti-sense sequences for specific recognition, and an RNA-cleaving enzymatic activity. "Ribozyme gene" refers to a nucleic acid molecule (e.g., DNA) consisting of the ribozyme sequence which, when transcribed into RNA, will yield the ribozyme.

"Vector" refers to an assembly which is capable of expressing a ribozyme of interest. The vector may be composed of either deoxyribonucleic acids ("DNA") or ribonucleic acids ("RNA"). Optionally, the vector may include a polyadenylation sequence, one or more restriction sites, as well as one or more selectable markers such as neomycin phosphotransferase, hygromycin phosphotransferase or puromycin-N-acetyl-transferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

As noted above, the present invention provides ribozymes which are capable of cleaving Hepatitis C Virus nucleic acids. Briefly, the viral genome of HCV has an approximately 9.5 Kb linear genome that replicates through a double stranded RNA intermediate (Choo et al., *Proc. Natl. Acad. Sci. USA* 88:2451–2455, 1991; Choo et al., *Brit. Med. Bull.* 46(2):423–441, 1990; Okamoto et al., *J. Gen. Vir.* 72:2697–2704, 1991; see also, e.g., Genbank Accession No. M67463, Intelligenetics (Mountain View, Calif.). This sequence expresses a polyprotein precursor of 3011 amino acids, which is cleaved to yield several different viral proteins, including C (nucleocapsid protein) E1, E2/NS1, and non-structural proteins NS2, NS3, NS4, and NS5 (Houghton et al., *Hepatology* 14:381–388, 1991).

Sequence analyses of HCV isolates indicate considerable sequence variation (for reviews see Houghton et al., *Hepatology* 14:381–388, 1991; van Doorn, *J. Med. Virology* 43:345–356, 1994; Bukh et al., *Seminars in Liver Disease* 15:41–63, 1995; Simmonds, *Hepatology* 21:570–583, 1995;

see also Genbank Assession Nos. D10749, D10750, D11168, D11355, D13558, D30613, D90208, L02836, M58335, M84754, M96362, S62220, U01214, U16362, X61596). The most conserved regions (>90% sequence identity within the known isolates) reside within the first 1000 nucleotides of the genome, which consists of a 5' untranslated region (5'UTR) and the coding region for the nucleocapsid (Bukh et al., *Proc. Natl. Acad. Sci. USA* 89:4942–4946, 1992). The highest degree of sequence variability (up to 50% sequence divergence) is found within the E1 and NS2 genes (see above reviews). Based on this sequence heterogeneity, HCV isolates can be categorized into at least 12 distinct genotypes (Okamoto et al., *Virology* 188:331–341, 1992; Bukh, et al., *Proc. Natl. Acad. Sci. USA* 90:8234–8238, 1993). Although most of the HCV genotypes are distributed worldwide, certain strains are found in discrete geographical regions (Bukh, et al., *Proc. Natl. Acad. Sci. USA* 90:8234–8238, 1993) and their distribution may play a role in ribozyme-mediated therapy.

Ribozymes

As noted above, the present invention provides ribozymes having the ability to inhibit replication, infectivity, or gene expression of a hepatitis C viral infection in a cell. Several different types of ribozymes may be constructed for use within the present invention, including for example, hammerhead ribozymes (Rossi, J. J. et al., *Pharmac. Ther.* 50:245–254, 1991) (Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988; Haseloff et al., U.S. Pat. No. 5,254,678), hairpin ribozymes (Hampel et al., *Nucl. Acids Res.* 18:299–304, 1990, and U.S. Pat. No. 5,254,678), hepatitis delta virus ribozymes (Perrotta and Been, *Biochem.* 31:16, 1992), Group I intron ribozymes (Cech et al., U.S. Pat. No. 4,987,071) and RNase P ribozymes (Takada et al., *Cell* 35:849, 1983); (see also, WO 95/29241, entitled "Ribozymes with Product Ejection by Strand Displacement"; and WO 95/31551, entitled "Novel Enzymatic RNA Molecules."

Cech et al. (U.S. Pat. No. 4,987,071, issued Jan. 22, 1991) has disclosed the preparation and use of ribozymes which are based on the properties of the Tetrahymena ribosomal RNA self-splicing reaction. These ribozymes require an eight base pair target site and free guanosine (or guanosine derivatives). A temperature optimum of 50° C. is reported for the endoribonuclease activity. The fragments that arise from cleavage contain 5'-phosphate and 3'-hydroxyl groups and a free guanosine nucleotide added to the 5'-end of the cleaved RNA.

In contrast to the ribozymes of Cech et al., particularly preferred ribozymes of the present invention hybridize efficiently to target sequences at physiological temperatures, making them suitable for use in vivo, and not merely as research tools (see column 15, lines 18 to 42, of Cech et al., U.S. Pat. No. 4,987,071). Thus, particularly preferred ribozymes for use within the present invention include hairpin ribozymes (for example, as described by Hampel et al., European Patent Publication No. 0 360 257, published Mar. 26, 1990) and hammerhead ribozymes. Briefly, the sequence requirement for the hairpin ribozyme is any RNA sequence consisting of NNNBN*GUC(N)$_x$ (Sequence ID Nos. 1–5) (where x is any number from 6 to 10, N*G is the cleavage site, B is any of G, C, or U, and N is any of G, U, C, or A). Representative examples of recognition or target sequences for hairpin ribozymes are set forth below in the Examples. Additionally, the backbone or common region of the hairpin ribozyme can be designed using the nucleotide sequence of the native hairpin ribozyme (Hampel et al., *Nucl. Acids Res.* 18:299–304, 1990) or it can be modified to include a "tetraloop" structure that increases stability and catalytic activity (see Example 2 and FIG. 3; see also Yu et al., *Virology* 206:381–386, 1995; Cheong et al., *Nature* 346:680–682, 1990; Anderson et al., *Nucl. Acids Res.* 22:1096–1100, 1994). The sequence requirement at the cleavage site for the hammerhead ribozyme is any RNA sequence consisting of NUX (where N is any of G, U, C, or A and X represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al., *Biochemistry* 29:10695–10702, 1990). This information, along with the sequences and disclosure provided herein, enables the production of hairpin ribozymes of this invention. Appropriate base changes in the ribozyme are made to maintain the necessary base pairing with the target HCV sequences.

The ribozymes of this invention, as well as DNA encoding such ribozymes and other suitable nucleic acid molecules, described in more detail below, can be chemically synthesized using methods well known in the art for the synthesis of nucleic acid molecules (see e.g., Heidenreich et al., *J. FASEB* 70(1):90–6, 1993; Sproat, *Curr. Opin. Biotechnol.* 4(1):20–28, 1993). Alternatively, commercial suppliers such as Promega, Madison, Wis., USA, provide a series of protocols suitable for the production of nucleic acid molecules such as ribozymes.

Within one aspect of the present invention, ribozymes are prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation with the RNA polymerase and appropriate nucleotides. In a separate embodiment, the DNA may be inserted into an expression cassette, such as described in Cotten and Birnstiel, *EMBO J.* 8(12):3861–3866, 1989, and in Hempel et al., *Biochemistry* 28:4929–4933, 1989. A more detailed discussion of molecular biology methodology is disclosed in Sambrook et al., *Molecular Cloning: A Laboratory Manual*, Cold Spring Harbor Press, 1989.

During synthesis, the ribozyme can be modified by ligation to a DNA molecule having the ability to stabilize the ribozyme and make it resistant to RNase (Rossi et al., *Pharmac. Ther.* 50:245–254, 1991). Alternatively, the ribozyme can be modified to a phosphothio-analog for use in liposome delivery systems. This modification also renders the ribozyme resistant to endonuclease activity.

Vectors

Use of ribozymes to treat HCV infection involves introduction of functional ribozyme to the infected cell of interest. This can be accomplished by either synthesizing functional ribozyme in vitro prior to delivery, or, by delivery of DNA capable of driving ribozyme synthesis in vivo.

More specifically, within other aspects of the invention the ribozyme gene may be constructed within a vector which is suitable for introduction to a host cell (e.g., prokaryotic or eukaryotic cells in culture or in the cells of an organism). Appropriate prokaryotic and eukaryotic cells can be transfected with an appropriate transfer vector containing the nucleic acid molecule encoding a ribozyme of this invention.

To produce the ribozymes with a vector in vivo, nucleotide sequences coding for ribozymes are preferably placed under the control of a eukaryotic promoter such as pol III (e.g., tRNA or VA-1 from adenovirus), CMV, SV40 late, or SV40 early promoters. Within certain embodiments, the promoter may be a tissue-specific promoter such as, for example, a liver-specific promoter such as the albumin promoter and the alphafetoprotein promoter (Feuerman et al., *Mol. Cell. Biol.* 9:4204–12, 1989; Camper and Tilghman, *Genes Develop.* 3:537–46, 1989); the alcohol dehydrogenase promoter (Felder, *Proc. Natl. Acad. Sci. USA* 86:5903–07, 1989); the Apolipoprotein B gene promoter (Das et al., *J. Biol. Chem.* 263:11452–8, 1988); the Coagulation protease factor VII gene promoter (Erdmann et al., *J. Biol. Chem.* 270:22988–96, 1995); the Fibrinogen gamma gene promoter (Zhang et al., *J. Biol. Chem.* 270:24287–91, 1995); the Glucokinase gene promoter (Williams et al., *Biochem. Biophys., Res. Comm.* 212:272–9, 1995); the Liver phosphofructokinase gene promoter (Levanon et al., *Biochem. Mol. Biol. Int.* 35:729–36, 1995); the Phospho-Enol-Pyruvate Carboxy-Kinase ("PEPCK") promoter (Hatzogiou et al., *J. Biol. Chem.* 263: 17798–808, 1988; Benvenisty et al., *Proc. Natl. Acad. Sci. USA* 86:1118–22, 1989; Vaulont et al., *Mol. Cell. Biol.* 9:4409–15, 1989); or lymphoid-specific promoters. Ribozymes may thus be produced directly from the transfer vector in vivo.

A wide variety of vectors may be utilized within the context of the present invention, including for example, plasmids, viruses, retrotransposons and cosmids. Because HCV is an acute or chronic infection of the liver, vectors with hepatotrophic properties are particularly preferred. Representative examples include adenoviral vectors (e.g., WO 94/26914, WO 93/9191; Yei et al., *Gene Therapy* 1:192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218). For vectors without inherent hepatotropism (e.g., AAV or retroviruses), cell tropism can be altered to specifically target these viruses to the liver. Methods of using such vectors in gene therapy are well known in the art, see, for example, Larrick, J. W. and Burck, K. L., *Gene Therapy. Application of Molecular Biology*, Elsevier Science Publishing Co., Inc., New York, N.Y., 1991 and Kreigler, M., *Gene Transfer and Expression: A Laboratory Manual*, W. H. Freeman and Company, New York, 1990.

Further provided by this invention are vectors having more than one nucleic acid molecule encoding a ribozyme of this invention, each molecule under the control of a separate eukaryotic promoter (or, an Internal Ribosome Entry Site or "IRES") or alternatively, under the control of single eukaryotic promoter. Representative examples of other nucleic acid molecules which may be delivered by the vectors of the present invention include therapeutic molecules such as interferon (e.g., alpha, beta or gamma), as well as a wide variety of other cytokines or growth factors, and facilitators which assist or aid ribozymes in cleaving a target sequence by unwinding or otherwise limiting secondary folding which might otherwise inhibit the ribozyme (see Example 4). These vectors provide the advantage of providing multi-functional therapy against HCV infection, preferably with the various therapies working together in synergy.

Host prokaryotic and eukaryotic cells stably harboring the vectors described above also are provided by this invention. Suitable host cells include bacterial cells, rat cells, mouse cells, and human cells, for example, liver and blood cells.

Delivery

Within certain aspects of the invention, ribozyme molecules, or nucleic acid molecules which encode the ribozyme, may be introduced into a host cell utilizing a vehicle, or by various physical methods. Representative examples of such methods include transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413–7417, 1989), microprojectile bombardment (Williams et al., *PNAS* 88:2726–2730, 1991), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al, *J. of Biol. Chem.* 264:16985–16987, 1989). In one embodiment, the ribozyme is introduced into the host cell using a liposome.

Within further embodiments of the invention, additional therapeutic molecules (e.g., interferon) or facilitators may be delivered utilizing the methods described herein. Such delivery may be either simultaneous to, or before or after the delivery of a ribozyme or vector expressing ribozymes.

Pharmaceutical Compositions

As noted above, pharmaceutical compositions also are provided by this invention. These compositions contain any of the above described ribozymes, DNA molecules, vectors or host cells, along with a pharmaceutically or physiologically acceptable carrier, excipient, or, diluent. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

Pharmaceutical compositions of the present invention may also be prepared to contain, or express (e.g., if a vector), one or more additional therapeutic molecules (e.g., interferon) or facilitators.

In addition, the pharmaceutical compositions of the present invention may be prepared for administration by a variety of different routes, including for example intraarticularly, intracranially, intradermally, intrahepatically, intramuscularly, intraocularly, intraperitoneally, intrathecally, intravenously (e.g., into the protal vein), or subcutaneously. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition Pharmaceutical compositions are useful for both diagnostic or therapeutic purposes.

Therapeutic Methods

Methods of interfering with or preventing HCV viral replication, infectivity, or gene expression in a cell infected with HCV are also provided by this invention. Such methods require contacting the cell with an effective amount of ribozyme of this invention or, alternatively, by transducing the cell with an effective amount of vector having a nucleic acid molecule encoding the ribozyme. Effective amounts can be readily determined by those of skill in the art using well known methodology. When exogenously delivering the ribozyme, the RNA molecule can be embedded within a stable RNA molecule or in another form of protective environment, such as a liposome. Alternatively, the RNA can be embedded within RNase-resistant DNA counterparts. Cellular uptake of the exogenous ribozyme can be enhanced by attaching chemical groups to the DNA ends, such as cholesteryl moieties (Letsinger et al., P.N.A.S., U.S.A., 1989).

In another aspect of the invention, the target cell is transduced under conditions favoring insertion of the vector into the target cell and stable expression of the nucleic acid encoding the HCV specific ribozyme. The target cell can include but is not limited to hepatocytes and lymphocytes. If the cell is transduced prior to HCV infection, infection of the target cell or its progeny can be prevented. Accordingly, this aspect includes methods for interfering with or preventing HCV viral infection and/or replication in a cell by reacting the target RNA sequence with a ribozyme of this invention.

In one embodiment of this aspect of the invention, appropriate host cells such as liver cells are removed from a subject, e.g., a human patient, using methods well known in the art. The cells are then trypsinized and resuspended for ex vivo therapy. Within the cell or within the cells of an organism, a transfer vector as described above encoding one or more ribozymes is transfected into a cell or cells using methods described in Llewellyn et al., *J. Mol. Biol.* 195:115–123, 1987, and Hanahan, 166:557–580, 1983. Inside the cell, the transfer vector replicates and the DNA coding for the ribozyme is transcribed by cellular polymerases to produce ribozymes which then inactivate HCV. Micromanipulation techniques such as microinjection also can be used to insert the vector into the cell so that the transfer vector or a part thereof is integrated into the genome of the cell. Transcription of the integrated material gives rise to ribozymes which then inactivate HCV. The above methods are not intended to limit the invention, but merely to exemplify various means to effect the ribozyme therapy of this invention. Other methods are detailed in Anderson, *Science* 256:808–813, 1992.

For ex vivo therapy, the transduced cells can be reintroduced into the patient by hepatic artery injection under conditions such that the transduced cells will integrate into the liver.

As used herein, the term "interfering with or preventing" HCV viral replication in a cell means to reduce HCV replication or production of HCV components necessary for progeny virus in a cell as compared to a cell not being transiently or stably transduced with the ribozyme or a vector encoding the ribozyme. Simple and convenient assays to determine if HCV viral replication has been reduced include an ELISA assay for the presence, absence, or reduced presence of anti-HCV antibodies in the blood of the subject (Nasoff et al., *PNAS* 88:5462–5466, 1991), RT-PCR (Yu et al., in *Viral Hepatitis and Liver Disease* 574–477, Nishioka, Suzuki and Mishiro (Eds.); Springer-Verlag Tokyo, 1994) or liver function tests. Such methods are well known to those of ordinary skill in the art. Alternatively, total RNA from transduced and infected "control" cells can be isolated and subjected to analysis by dot blot or northern blot and probed with HCV specific DNA to determine if HCV replication is reduced. Alternatively, reduction of HCV protein expression can also be used as an indicator of inhibition of HCV replication. A greater than fifty percent reduction in HCV replication as compared to control cells typically quantitates a prevention of HCV replication.

Diagnostic Methods

Detection and diagnosis of hepatitis C infection in humans has been somewhat problematic to date. The most commonly used methods involve detection of antibodies produced by the host against HCV structural proteins. Unfortunately, many patients remain seronegative for a variable length of time and frequently the eventual immune response can be difficult to detect. Furthermore, due to the considerable sequence variation in the HCV genome and mutations in the structural proteins, host-produced antibodies can vary significantly, requiring a large panel of antigens for accurate detection. For these reasons, a more reliable method for detection of infectious HCV would be useful, not only to test patient serum but also to screen the multitude of human-derived blood products purified for medical use.

HCV hairpin ribozymes can be applied to the detection and diagnosis of HCV infection. To accomplish this, a special reporter plasmid is generated which contains the HCV 5'-capsid sequence upstream of the *E. coli* lacZ gene (nucleotides 1302–4358, Genbank accession no. J01636). This plasmid is made via a two-step cloning process. First, HCV sequences containing the 5' UTR and capsid coding region are synthesized directly from RNA that was extracted from an HCV-positive patient serum sample. The purified viral RNA is then reverse transcribed and PCR amplified with the following primers: sense (starting at 5' end of 5' UTR) 5'-GCCAGCCCCC TGATGGGG-3' (Sequence ID No. 6) and antisense (starting at 3' end of capsid coding region) 5'-CACCTGATAA GCGGAAGC-3' (Sequence ID No. 7). The resulting blunt-end DNA is then ligated the unique Sma I site in pCMVβ (Clontech, Palo Alto, Calif.). This first generation plasmid is designated pCMV-HCV-β. Second, to allow selection of this plasmid following transfection into mammalian cells, a neomycin resistance expression cassette, consisting of the SV40 early promoter driving the expression of the neomycin resistance gene, is constructed. This is accomplished by blunt-ligating a BamHI fragment, containing the neomycin cassette obtained from pMAMneo-LUC (Clontech, Palo Alto, Calif.), into the unique SalI site of pCMV-HCV-β. The resulting plasmid, pCMV-HCV-β-SV-neo expresses two independent RNAs. One containing the HCV target sites upstream of the lacZ coding sequence, and the other expressing neomycin resistance for positive selection.

To generate the reporter cell line, the human hepatocellular carcinoma cell line Huh7 (Yoo et al., *J. Virol.* 69:32–38, 1995), is co-transfected with pCMV-HCV-β-SV-neo and an HCV hairpin ribozyme expression plasmid, pLNT-Rz. G418-selected transfected Huh7 cells, containing both Rz and reporter plasmids, is then used for HCV infection diagnosis. Under normal conditions, expressed HCV Rz will cleave the HCV 5'UTR-capsid target located on the lacZ mRNA, resulting in the inhibition of β-galactosidase expression. When cells are challenged with a biological sample (e g., patient serum samples or other blood products containing HCV, or tissue or cell samples taken from the liver), the presence of the HCV 5'UTR-capsid sequences coming from the replicating HCV will compete for the ribozyme, interfering with its ability to cleave the HCV-lacZ RNA. The result of this interference in Rz activity is an increased expression of β-galactosidase and these cells will stain blue by routine lacZ staining. Thus, any patient serum (or other biological sample) which is positive for hepatitis C virus will cause these reporter cells to turn blue.

The following examples are offered by way of illustration, and not by way of limitation.

EXAMPLES

Example 1

Criteria For Hairpin Ribozyme Site Selection

Hairpin ribozymes suitable for use within the present invention preferably recognize the following sequence of RNA: NNNBNGUC(N)$_x$ (Sequence ID Nos. 1–5) wherein the ribozyme is constructed so as to be complementary to the underlined sequences, and wherein B is C, G or U, and x is from 6 to 10 nucleotides. The sequence GUC must be conserved for all hairpin ribozymes described below. Other nucleotides ("N" as underlined above) preferably have a high degree of sequence conservation among different HCV strains in order to limit the need for multiple ribozymes against the same target site.

Briefly, sequence analysis of the complete genome of HCV-1 reveals 112 suitable GUC hairpin ribozyme sites in the positive strand and 125 suitable sites in the negative strand. Due to the considerable sequence variability between different HCV genotypes, however, only 34 sites in the positive strand and 36 in the negative strand represent GUC's that are 95% conserved between all known strains. The nucleotides flanking the GUC (represented as "N" above) should also preferably contain a high degree of sequence conservation in order to limit the need to design multiple ribozymes against the same target site. To that end, 28 sites have been identified in the positive strand and 30 sites in the negative strand that have no more than one base mismatch in >85% of the known strains. These sites are provided below in Table I:

TABLE I

Hepatitis C Ribozymes Directed Against Both (+) and (−) Strand RNA

| RIBOZYME: | RECOGNITION SEQUENCE[a]: | LOCATION[b]: | WITHIN: | SEQ. I.D. |
|---|---|---|---|---|
| HCV-1 (+) STRAND: | | | | |
| CR1 | ACCGG^GUCCUUUCUUG | 190 | 5'UTR | 8 |
| CR2 | UAGUG^GUCUGCGGAAC | 146 | 5'UTR | 9 |
| CR3 | CGGUG^GUCAGAUCGUU | 424 | Capsid | 10 |
| CR4 | GAGCG^GUCGCAACCUC | 506 | Capsid | 11 |
| CR4-7 | GAGCG^GUCGCAACCU | 506 | Capsid | 12 |
| CR4-6 | GAGCG^GUCGCAACC | 506 | Capsid | 13 |
| CR5 | CUCCU^GUCACCCCGCG | 635 | Capsid | 14 |
| CR6 | CUACU^GUCUUCACGCA | 60 | 5'UTR | 15 |
| CR7 | AAAGC^GUCUAGCCAUG | 77 | 5'UTR | 16 |
| CR8 | UGAGU^GUCGUGCAGCC | 102 | 5'UTR | 17 |
| CR9 | GUUGG^GUCGCGAAAGG | 268 | 5'UTR | 18 |
| CR10 | CGCUC^GUCGGCGQCCC | 759 | Capsid | 19 |
| CR11 | AACUG^GUCGCCUACAA | 1319 | E1 | 20 |
| CR12 | AUAGG^GUCAGCGGUUG | 2459 | NS1 | 21 |
| CR13 | ACCUU^GUCACCACACU | 2834 | NS2 | 22 |
| CR14 | AUGCG^GUCCCCGGUCU | 3958 | NS3 | 23 |
| CR15 | CCCCG^GUCUUCACGGA | 3965 | NS3 | 24 |
| CR16 | GACGU^GUCCGUCAUAC | 4610 | NS3 | 25 |
| CR17 | CAUGU^GUCACCCAGAC | 4712 | NS3 | 26 |
| CR18 | AGACA^GUCGAUUUCAG | 4724 | NS3 | 27 |
| CR19 | GCGGU^GUCGCGCUCAC | 4787 | NS3 | 28 |
| CR20 | AGGUC^GUCACUAGCAC | 5307 | NS4 | 29 |
| CR21 | CUCCA^GUCCAAGCUCC | 6329 | NS4 | 30 |
| CR22 | GUUGA^GUCGUACUCCU | 7491 | NS5 | 31 |
| CR23 | UCUUG^GUCUACCGUGA | 7556 | NS5 | 32 |
| CR24 | ACAUG^GUCUAUGCCAC | 7707 | NS5 | 33 |
| CR25 | AAGGC^GUCCACAGUUA | 7823 | NS5 | 34 |
| CR26 | ACGUG^GUCUCCACCCU | 8133 | NS5 | 35 |

TABLE I-continued

Hepatitis C Ribozymes Directed Against Both (+) and (−) Strand RNA

| RIBOZYME: | RECOGNITION SEQUENCE[a]: | LOCATION[b] | WITHIN: | SEQ. I.D. |
|---|---|---|---|---|
| CR27 | GGCCU^GUCGAGCUGCA | 8506 | NS5 | 36 |
| CR28 | CUACU^GUCCCAAGGGG | 9134 | NS5 | 37 |
| HCV-1 (−) STRAND: | | | | |
| CNR1 | GGAGU^GUCGCCCCCAA | 23 | "5'UTR" | 38 |
| CNR2 | GGGGG^GUCCUGGAGGC | 120 | "5'UTR" | 39 |
| CNR3 | CGGUC^GUCCUGGCAAU | 183 | "5'UTR" | 40 |
| CNR4 | ACCCG^GUCGUCCAGGC | 186 | "5'UTR" | 41 |
| CNR5 | UAGCA^GUCUCGCGGGG | 247 | "5'UTR" | 42 |
| CNR6 | GCACG^GUCUACGAGAC | 333 | "5'UTR" | 43 |
| CNR7 | CGGGG^GUCCGUGGGGC | 674 | "Capsid" | 44 |
| CNR8 | ACGCC^GUCCUCCAGAA | 821 | "Capsid" | 45 |
| CNR9 | GAGCA^GUCAUUCGUGA | 959 | "E1" | 46 |
| CNR10 | GCGGU^GUCCGCCCCCC | 3308 | "NS2" | 47 |
| CNR11 | GUCGA^GUCAGUUGAGU | 4307 | "NS3" | 48 |
| CNR12 | CAGCC^GUCUCCGCUUG | 4354 | "NS3" | 49 |
| CNR13 | AGAGC^GUCUGUUGCCA | 4655 | "NS3" | 50 |
| CNR14 | UUGCA^GUCGAUCACCG | 4700 | "NS3" | 51 |
| CNR15 | CCCGC^GUCAUAGCACU | 4907 | "NS3" | 52 |
| CNR16 | GAGCA^GUCCUCAUUAA | 6242 | "NS4" | 53 |
| CNR17 | UACCC^GUCACGUAGUG | 6649 | "NS5" | 54 |
| CNR18 | ACGUU^GUCGGUGGUCA | 6665 | "NS5" | 55 |
| CNR19 | CAACC^GUCCUCUUUUU | 7336 | "NS5" | 56 |
| CNR20 | UCAGG^GUCCCCGGCU | 7532 | "NS5" | 57 |
| CNR21 | GACCC^GUCGCUGAGAU | 7547 | "NS5" | 58 |
| CNR22 | AGUCU^GUCAAAGGUGA | 7763 | "NS5" | 59 |
| CNR23 | GGGGC^GUCAGCUUGCA | 7873 | "NS5" | 60 |
| CNR24 | GUUGA^GUCAAAGCAGC | 8273 | "NS5" | 61 |
| CNR25 | AAUUA^GUCAGGGGGCC | 8398 | "NS5" | 62 |
| CNR26 | UAGUC^GUCAGCACGCC | 8455 | "NS5" | 63 |
| CNR27 | GUGCA^GUCCUGGAGCU | 8528 | "NS5" | 64 |
| CNR28 | ACCUA^GUCAUAGCCUC | 8629 | "NS5" | 65 |
| CNR29 | AGUGU^GUCUAGGUCUC | 8802 | "NS5" | 66 |
| CNR30 | GCGGG^GUCGGGCACGA | 9303 | "NS5" | 67 |

[a]Recognition sequence is written 5' to 3'. Cleavage occurs at ^
[b]Location indicates nucleotide position of cleavage site (the "G" in the "GUC") in either (+) strand, counting from 5' end, or (−) strand counting from 3' end. Numbering is using HCV-1 strain.

Example 2

Construction of Hairpin Ribozymes

Ribozyme genes (Rz) are designed by identifying highly sequence-conserved regions of the HCV genome that contain the obligatory GUC recognition signal. Rz's recognizing these sites are then designed on the basis of the nucleotide sequence adjacent to the GUC recognition signal. More specifically, two single-stranded DNA oligonucleotides are chemically synthesized such that, when combined and converted into double-stranded DNA, they contain the entire hairpin ribozyme, including nucleotides complementary to the target site. In addition, restriction enzyme recognition sites may be placed on either end to facilitate subsequent cloning.

For example, in order to construct ribozyme CR4, which recognizes the target sequence: GAGCGGUCGCAACCUC (Sequence I.D. No. 11; Table I), in either the native or tetraloop hairpin ribozyme structure (FIG. 3), the following oligonucleotides are prepared:

```
Sense oligo(Sequence I.D. No. 68):
        BamHI
    5'GCGGATCCGGAGGTTGCAGAAGCTCACCAGAGAAACACACG-3'

Universal antisense oligo(Sequence I.D. No. 69):
        MluI
    5'-GGGACGCGTACCAGGTAATATACCACAACGTGTGTTTCTCTGGT-3'

Universal tetraloop antisense oligo(Sequence I.D. No. 72):
        MluI
    5'-GGGACGCGTACCAGGTAATATACCACGGACCGAAGTCCGTGTGTTTCTC
    TGGT-3'
```

Restriction enzyme sites (BamH I and Mlu I) are indicated in italics. Sequences complementary to the CR4 target site in HCV are underlined. The 16 bases of complementary sequence to allow annealing between the sense oligo and either the universal antisense or the universal tetraloop antisense oligonucleotide are in bold.

Figure 2:
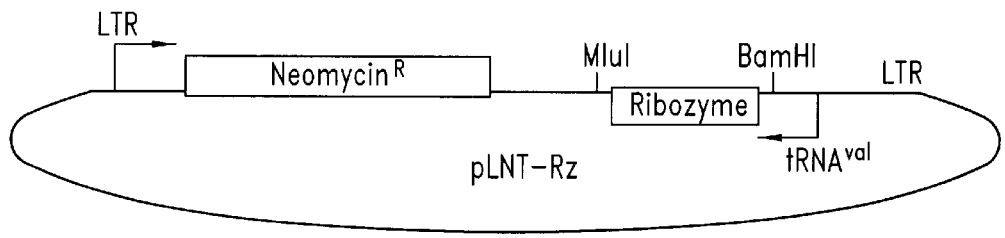
FIG. 2 is a schematic illustration of vector pLNT-Rz.

The appropriate oligonucleotides are annealed together and converted to double-stranded DNA using either Klenow DNA polymerase or Taq DNA polymerase. The resulting DNA is cleaved with restriction enzymes BamHI and MluI, purified and cloned into vectors for in vitro transcription (pGEM7Z, Promega, Madison, Wis.; FIG. 1) or for mammalian expression (pLNT; FIG. 2).

Figure 3:
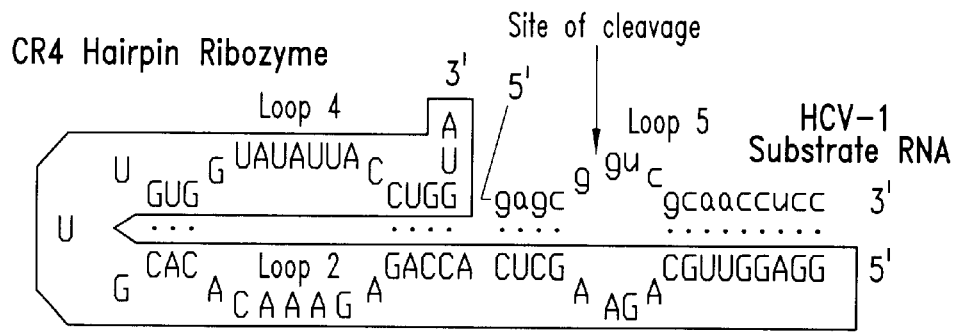
FIG. 3 is a schematic illustration of one representative hairpin ribozyme (Seq. ID Nos. 70 and 71) and one tetraloop hairpin ribozyme (CR4) (Seq. ID Nos. 73 and 71).
Figure 3:
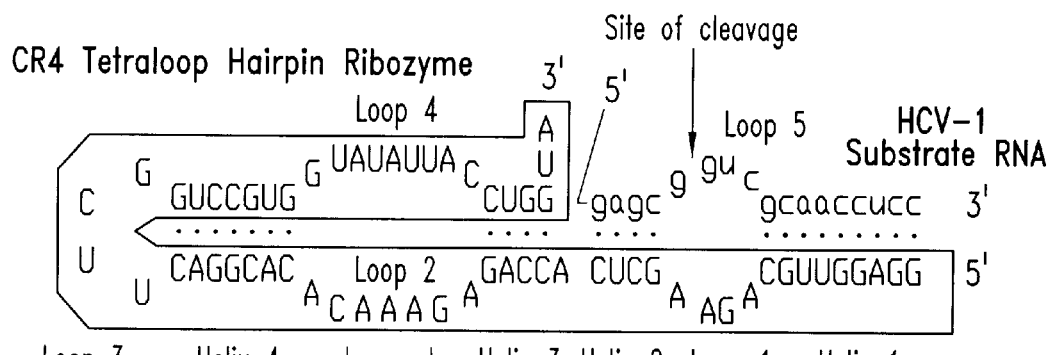

Defective ribozymes (referred to as "disabled") for use as controls may be constructed as described above, with the exception that the sequence AAA, in loop 2, is changed to a UGC as shown in FIG. 3.

Example 3

Construction of HCV Ribozyme Mammalian Expression Vectors

Plasmid pMJT (Yu et al., *Proc. Nat'l Acad. Sci. USA* 90:6340–6344, 1993; ATCC No. 75470), which contains the anti-U5 HIV ribozyme driven by the tRNA$^{val}$ RNA pol III promoter, is digested with BamHI and MluI, and the vector purified from the ribozyme fragment. The hepatitis C ribozyme genes, as described above, are excised from the pGem7Z vector (FIG. 1) with BamHI and MluI, purified, and ligated into the empty pMJT vector. The resulting vector is designated pLNT-Rz (see FIG. 2), and contains the Moloney LTR driving the neomycin resistance gene and the tRNA$^{val}$ RNA pol III promoter driving expression of the ribozyme.

Example 4

In Vitro Cleavage Assays

Ribozyme genes are cloned into in vitro transcription vectors (pGEM-7Z, Promega, Madison, Wis.) and transcribed in vitro by T7 RNA polymerase. Following transcription, reactions are treated with DNase and the ribozymes are purified by denaturing polyacrylamide gel electrophoresis.

The HCV substrates are as follows: short 5'UTR substrate HCV-1 nucleotides 1–185, short capsid substrate HCV-1 nucleotides 331–698 and long substrate HCV-1 nucleotides 1–698. Substrates are transcribed in vitro in the presence [$\alpha$-$^{32}$P]UTP and purified by denaturing polyacrylamide gel electrophoresis. The in vitro cleavage reactions are carried out by incubating 40 nM ribozyme with 200 nM substrate at 37° C. for 0 to 60 minutes in 12 mM MgCl$_2$/2 Mm spermidine/40 mM Tris-HCl, pH 7.5. Reactions are terminated by the addition of loading buffer (7 M urea/bromophenol blue/xylene cyanol). Products of the cleavage reactions are resolved by electrophoresis on 15% acrylamide/7 M urea gels and analyzed by autoradiography.

Figure 4:
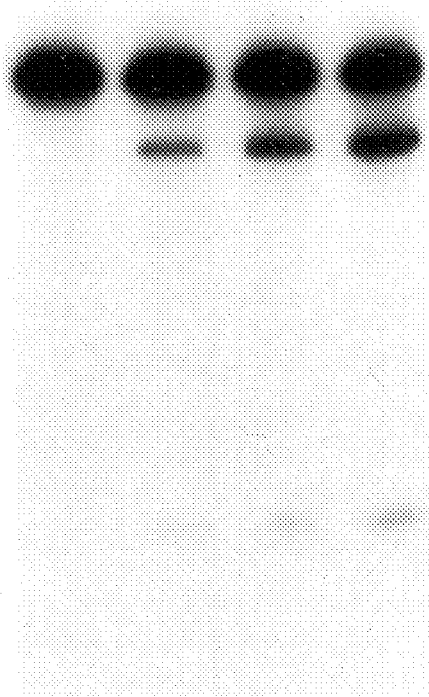
FIG. 4 is an in vitro cleavage timecourse of CR2 ribozyme cleaving the short 5'UTR substrate.

The data in FIG. 4 indicates that the CR2 Rz cleaves the short 5' UTR 185-nucleotide target RNA in a time dependent manner. Interestingly, the same Rz could not cleave a larger HCV RNA substrate that contained the entire 5' UTR (long HCV-1 substrate), presumably due to a highly folded secondary structure that is not present in the short substrate. In fact, the larger HCV substrate RNA could be cleaved by the Rz in vitro, only if the RNA substrate is heat denatured before the cleavage reaction (data not shown).

Occasionally, secondary structure in the target RNA is extensive enough to inhibit the binding and cleavage activities of hairpin ribozymes. One example is the 5'UTR of HCV, where RNA folding inhibits the activity of CR2. Thus, "facilitator" RNA molecules can be designed to enhance the activity of ribozymes targeted to highly folded structures. Briefly, facilitator molecules are RNA's that are engineered to be complimentary to regions of the target RNA flanking the ribozyme target site. When bound to the target RNA, these molecules help to relax the secondary structure, thus enhancing the binding, and therefore the activity, of the ribozyme.

Figure 5:
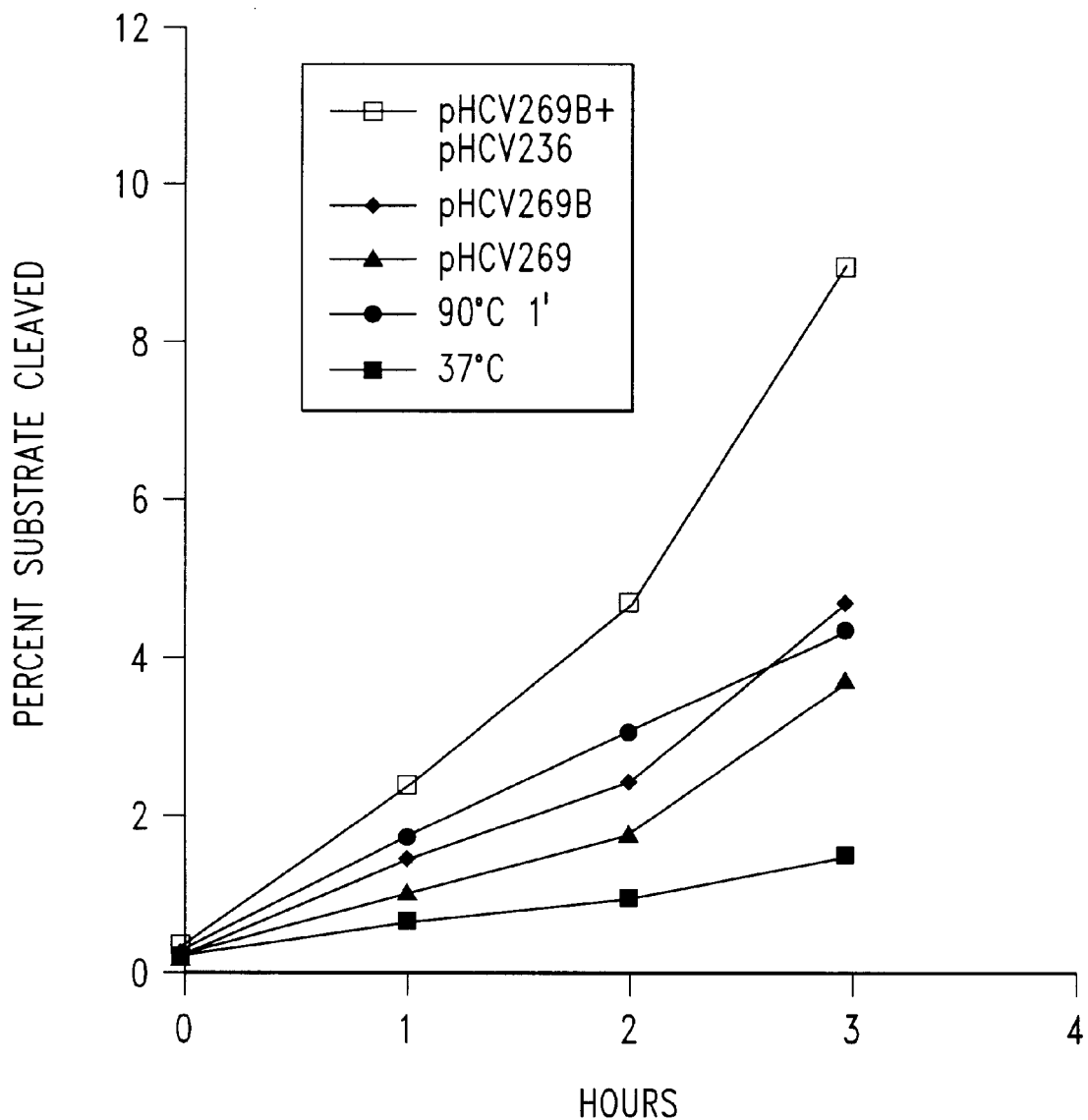
FIG. 5 is a graph which depicts in vitro cleavage timecourse reactions using CR2 and various facilitator RNA molecules, cleaving the long 5'UTR substrate.

Three facilitators are designed to disrupt the folded structure in the 5'UTR and were tested for their ability to enhance the activity of CR2. In particular, the following facilitators may be utilized: HCV269, HCV269B and HCV236 and are complimentary to bases 245–268, 242–268 and 217–235 of the 5' UTR of HCV-1 respectively. Facilitator RNAs are synthesized in vitro, added at a concentration of 40 nM to in vitro cleavage reactions containing CR2 and the long HCV-1 substrate, and cleavage reactions are monitored over 3 hours (FIG. 5). In the absence of any facilitator, less than 1% of the long HCV-1 substrate was cleaved over a period of 3 hours (FIG. 5, filled squares), consistent with previous results. Addition of either facilitator molecule, HCV269 or HCV269B, enhances the substrate cleavage 3- to 3.5-fold over the control (FIG. 5, filled triangles and filled diamonds). The stimulation seen with either single facilitator is similar to that seen for the reaction without facilitator, when ribozyme and substrate are heated to 90° C. for 1 minute prior to incubation at 37° C. (FIG. 5, filled circle). When the facilitators HCV269B and HCV236 are added in combination, the reaction was stimulated 9-fold over the control reaction (FIG. 5, open squares), indicating an additive to synergistic effect. These results indicate that ribozymes inhibited by secondary structure in the substrate (such as CR2) can become active against full length substrates when used with appropriately designed facilitator molecules.

Figure 6:
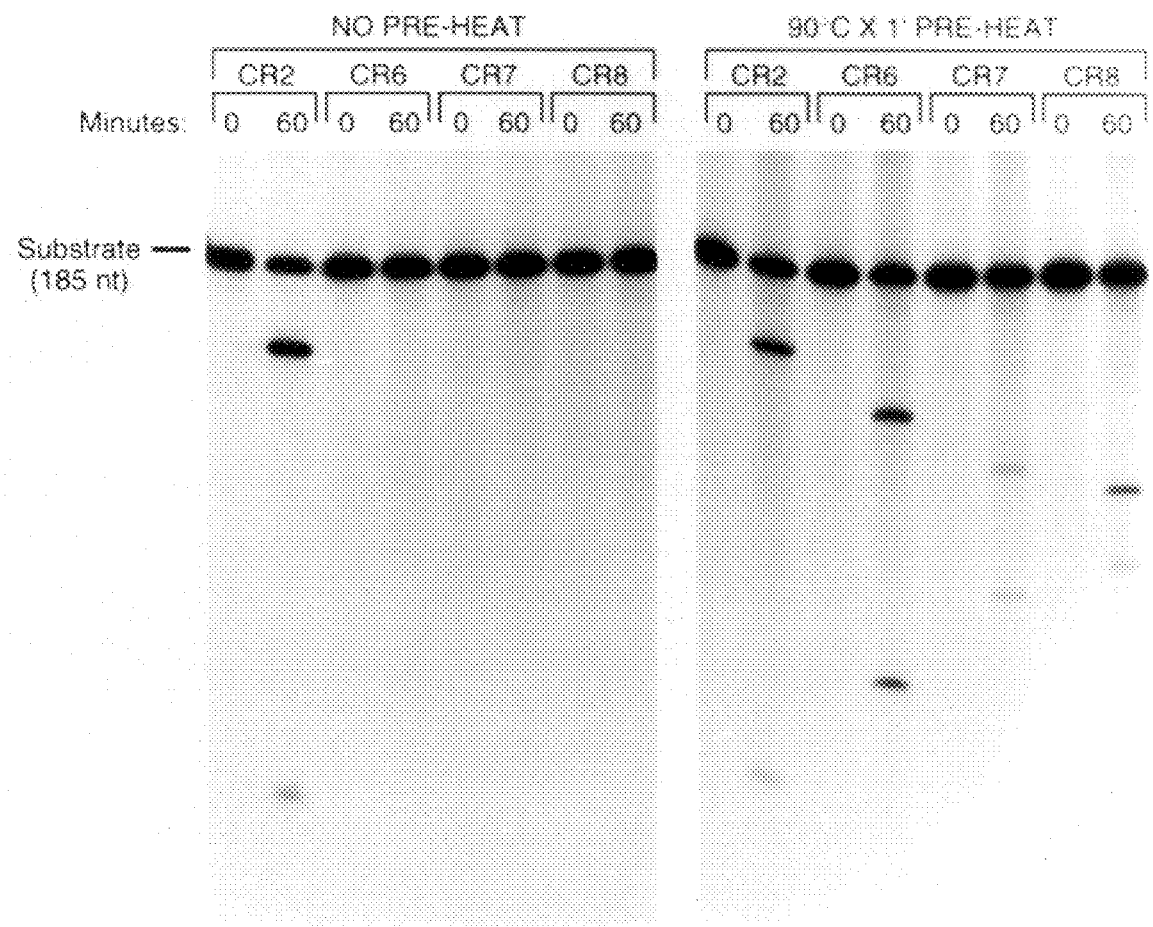
FIG. 6 depicts two in vitro cleavage experiments, one with and one without a pre-heating step of 90° C. for 1 minute prior to the cleavage reaction. Ribozymes tested are CR2, CR6, CR7 and CR8 using the short 5'UTR substrate.

Three additional Rz directed against the HCV 5' UTR (CR6, CR7, and CR8) are also tested on the 185-nucleotide short 5' UTR substrate. As indicated by the data in FIG. 6, these Rz could only cleave the short 5' UTR substrate when it is heat denatured, while cleavage of the short 5'UTR substrate by the CR2 Rz, as before, is independent of heat denaturation. Consistent with the role of secondary structure in the availability of RNA for Rz cleavage, the target sequences for CR6, CR7, and CR8 are in a location that allows extensive secondary structure, even in the short 5' UTR substrate.

Figure 7:
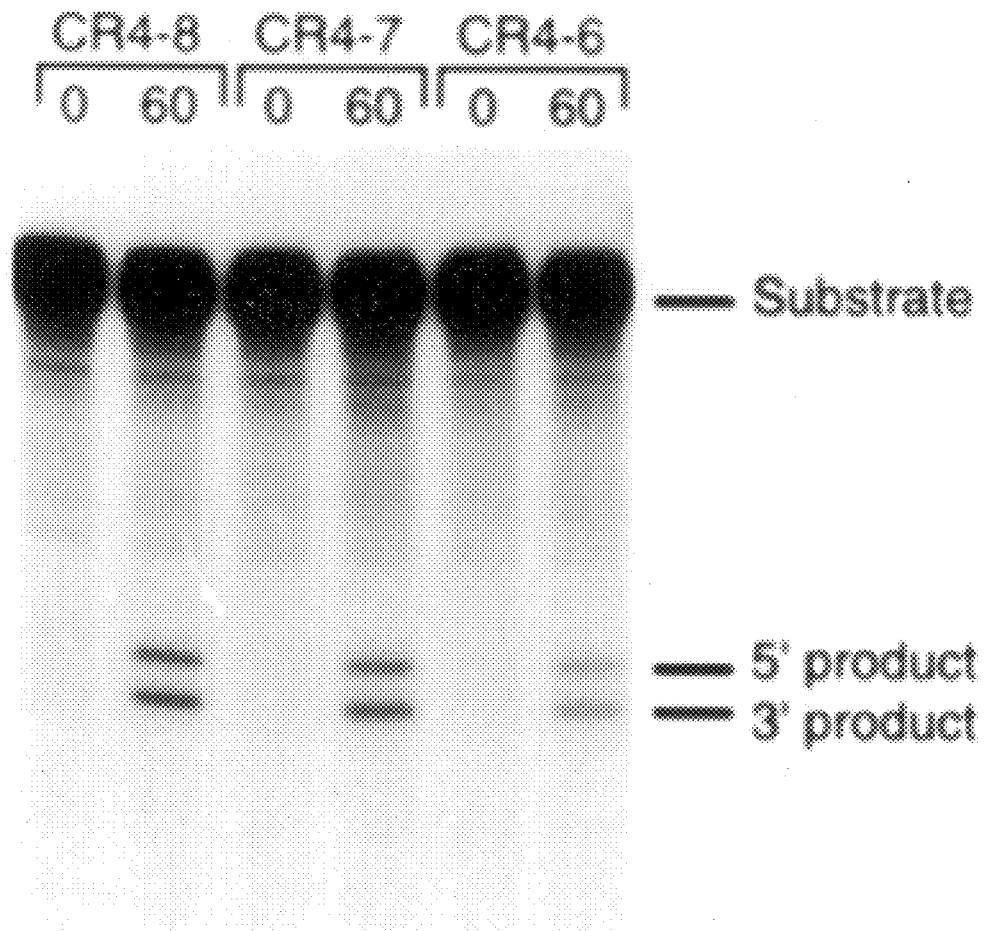
FIG. 7 shows in vitro cleavage reactions using variants of CR4 ribozyme with either 8, 7 or 6 nucleotides in Helix 1, using the short capsid substrate.

A potential Rz cleavage site in a highly conserved region of the HCV Capsid protein, not containing as much secondary structure as the 5' UTR, is next tested. Like the previously tested CR2 Rz, the Capsid-targeted CR4-8 Rz cleaves a short HCV capsid substrate RNA in vitro, without heat denaturation (FIG. 7). Since the catalytic efficiency of Rz may be limited by the dissociation constant, and thus the size of the target sequence recognized, ribozymes are also generated and tested that cleave the same site as CR4-8, but recognize a target sequence that lacks one nucleotide (CR4-7) or two nucleotides (CR4-6) compared with the CR4-8 Rz. This is accomplished by changing the length of Helix 1 (FIG. 3). The data in FIG. 7 indicate that CR4-7 and CR4-6 are not more active than CR4-8, in fact cleavage by CR4-8 may be more efficient.

Figure 8:
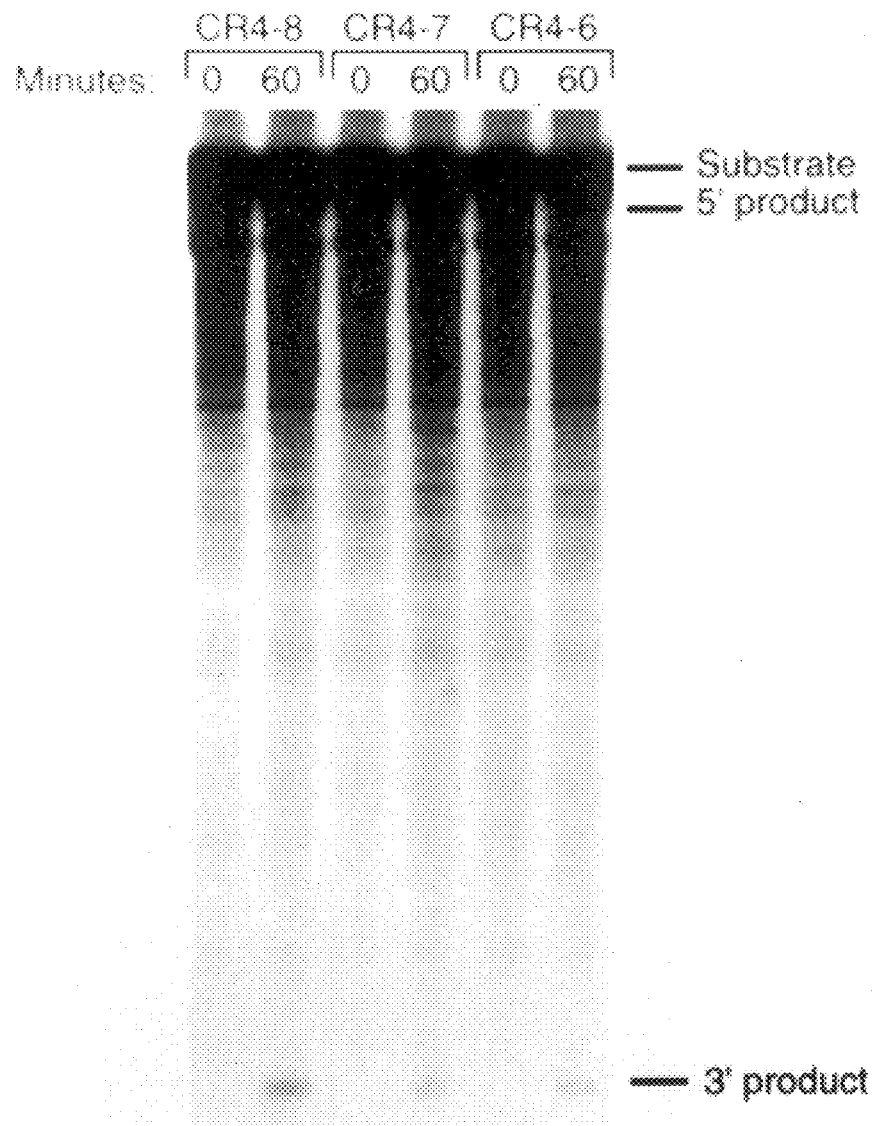
FIG. 8 depicts in vitro cleavage reactions using variants of CR4 ribozyme with either 8, 7 or 6 nucleotides in Helix 1 using the long capsid substrate.
Figure 9A:
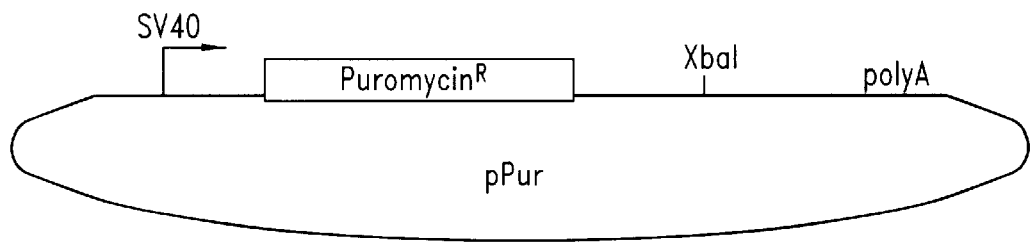
FIGS. 9A, 9B, 9C and 9D are schematic illustrations of certain vectors described herein: pPur, pPur-HCV, pLNL6 and pLNL-Pur-HCV.
Figure 9B:
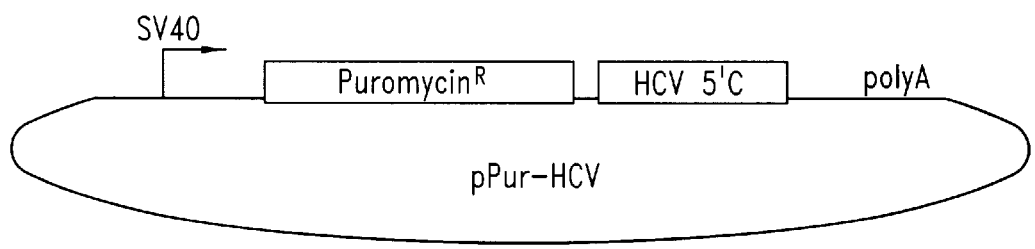
Figure 9C:
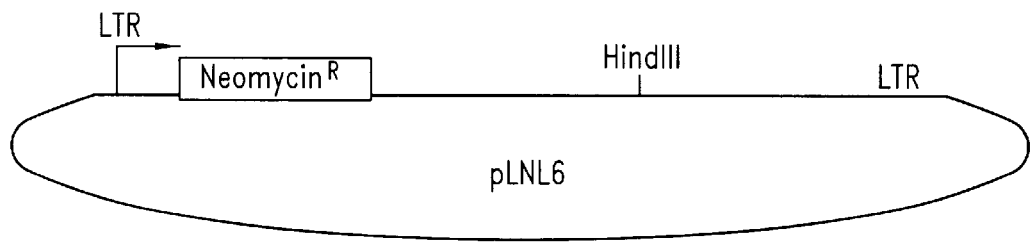
Figure 9D:
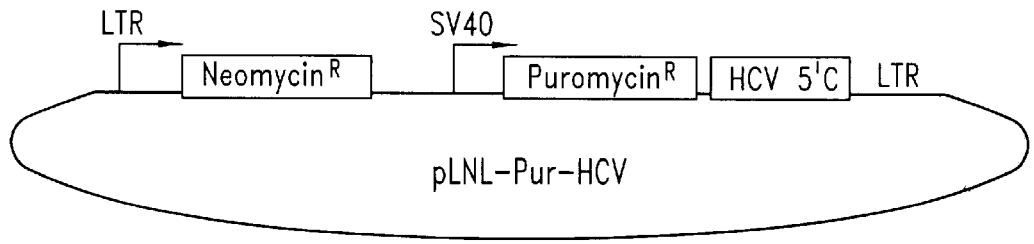

As indicated by the data in FIG. 8, CR-4 is capable of cleaving the long HCV substrate RNA, containing the extensive secondary structure, without heat denaturation. The autoradiogram in FIG. 8 is overexposed to reveal the low molecular weight cleavage product, but lighter exposures reveal the expected higher molecular weight fragment (additional exposure not shown). As with the short substrate, cleavage by CR4-8 is identical with, or slightly more effective than, that of either CR4-7 or CR4-6.

Example 5

Construction of Vectors, and Testing of Gene Expression in Tissue Culture

As described in more detail below, reporter systems are developed to evaluate the effect of Rz expression on the expression of genes containing HCV Rz target sequences.

A. Construction of Vectors

Construction of several expression vectors is described herein (FIG. 9). The HCV reporter plasmid pPur-HCV (FIG. 9B) is constructed as follows: HCV sequences containing the 5'UTR and capsid coding region are synthesized directly from RNA that is extracted from an HCV-positive patient serum sample. The purified viral RNA is then reverse transcribed and PCR amplified with the following primers: sense (starting at 5' end of 5' UTR) 5'-GCCAGCCCCC TGATGGGG-3' (Sequence ID No. 6) and antisense (starting at 3' end of capsid coding region) 5'-CACCTGATAA GCGGAAGC-3' (Sequence ID No. 7). The resulting blunt-end DNA is then ligated into plasmid pPur (Clontech, Palo Alto, Calif.; FIG. 9A) that has been digested with XbaI and blunt-ended with Klenow DNA polymerase. The HCV reporter retroviral vector pLNL-Pur-HCV (FIG. 9D) is constructed by purifying the 2065 bp PvuII/XbaI fragment from pPur-HCV, which contains the SV40 early promoter, the puromycin resistance coding region and the HCV 5'UTR and capsid sequences. The fragment is blunt-ended with Klenow and cloned into plasmid pLNL6 (Bender et al., *J. Virol.* 61:1639–1646, 1987; FIG. 9C) that has been digested with HindIII and blunt-ended with Klenow. Both resulting HCV reporter plasmids will then produce an RNA transcript, via SV40 early promoter, that contains the HCV 5' UTR and capsid sequences on the same RNA transcript as the coding region for puromycin resistance. Each HCV ribozyme is expressed on a separate retroviral vector (pLNT-Rz) via the tRNA$^{val}$ pol III promoter. Active HCV ribozymes will cleave the Pur-HCV RNA, resulting in a cell sensitive to puromycin.

B. Co-transfection and Assay of Ribozymes

The ability of Rz to inactivate RNA containing HCV sequences is determined by co-transfection of a Rz-expressing plasmid (pLNT-Rz) with plasmids expressing an mRNA that contains HCV target sequences and codes for puromycin resistance (pPur-HCV).

Figure 10:
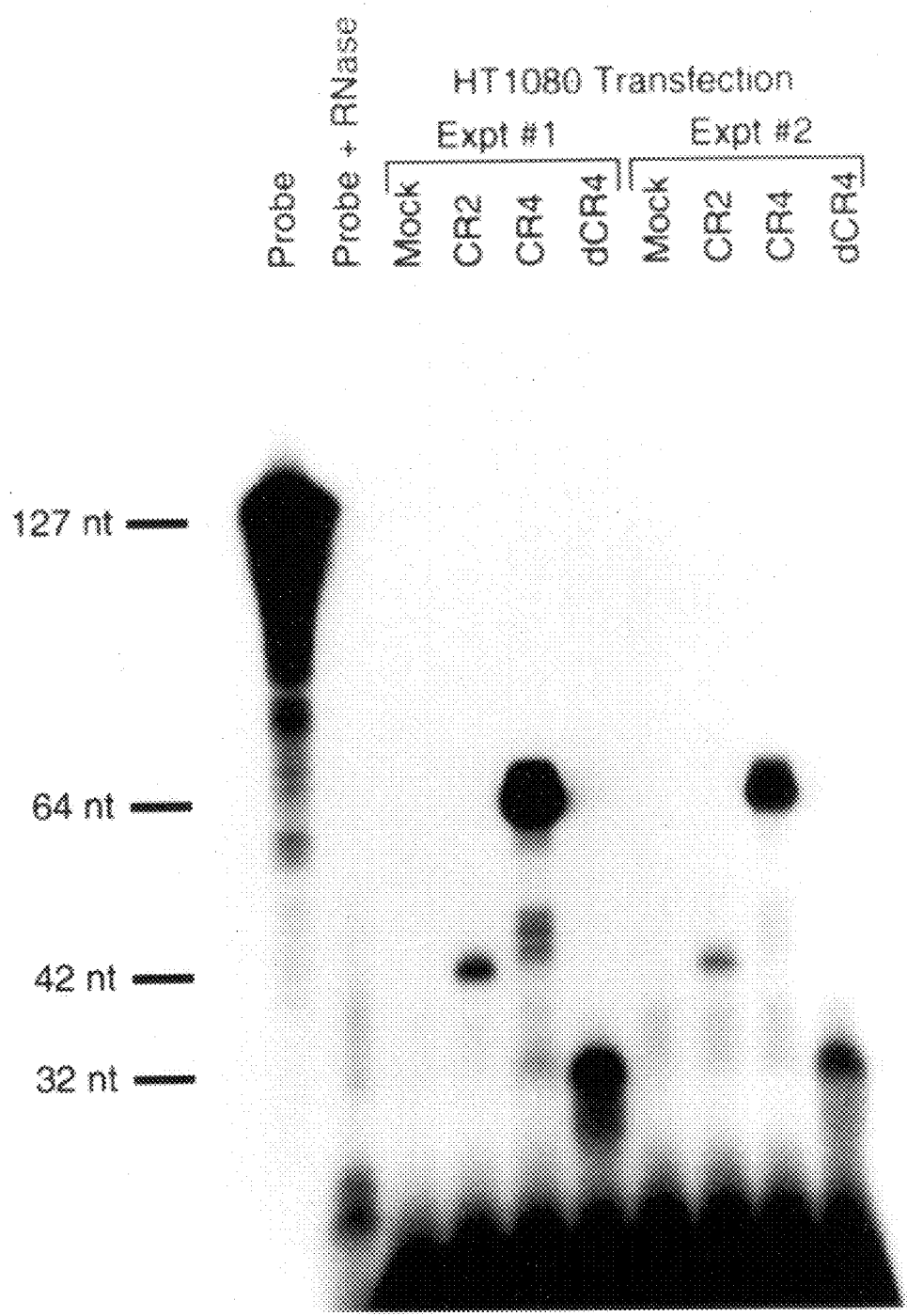
FIG. 10 is an RNase protection assay verifying ribozyme expression after transfection.

Briefly, HeLa or HT1080 cells are co-transfected with pPur-HCV and various pLNT-Rz constructs using standard calcium phosphate methods. DNA molar ratios for the HCV:Rz co-transfections is 1:10, using empty pLNT vector to maintain total DNA at 20 μg. Ribozymes tested included two anti-HCV ribozymes: CR2 (against the 5' UTR) and CR4 (against capsid), and one disabled anti-HBV ribozyme, dBR1, included as a negative control. Cells are selected with 1 μg/ml puromycin starting 24 hours post transfection, and continued for up to two weeks. Puromycin-resistant colonies are visualized by crystal violet staining and counted. Ribozyme expression within the transfected cells is verified by RNase protection. Using radiolabeled antisense CR4 RNA as the RNase protection probe, the expected protected fragments are 64 nt for CR4, 42 nt for CR2 and 32 nt for dCR4 (FIG. 10; RNase Protection Assay Kit is available from Promega, Madison, Wis.).

Figure 11A:
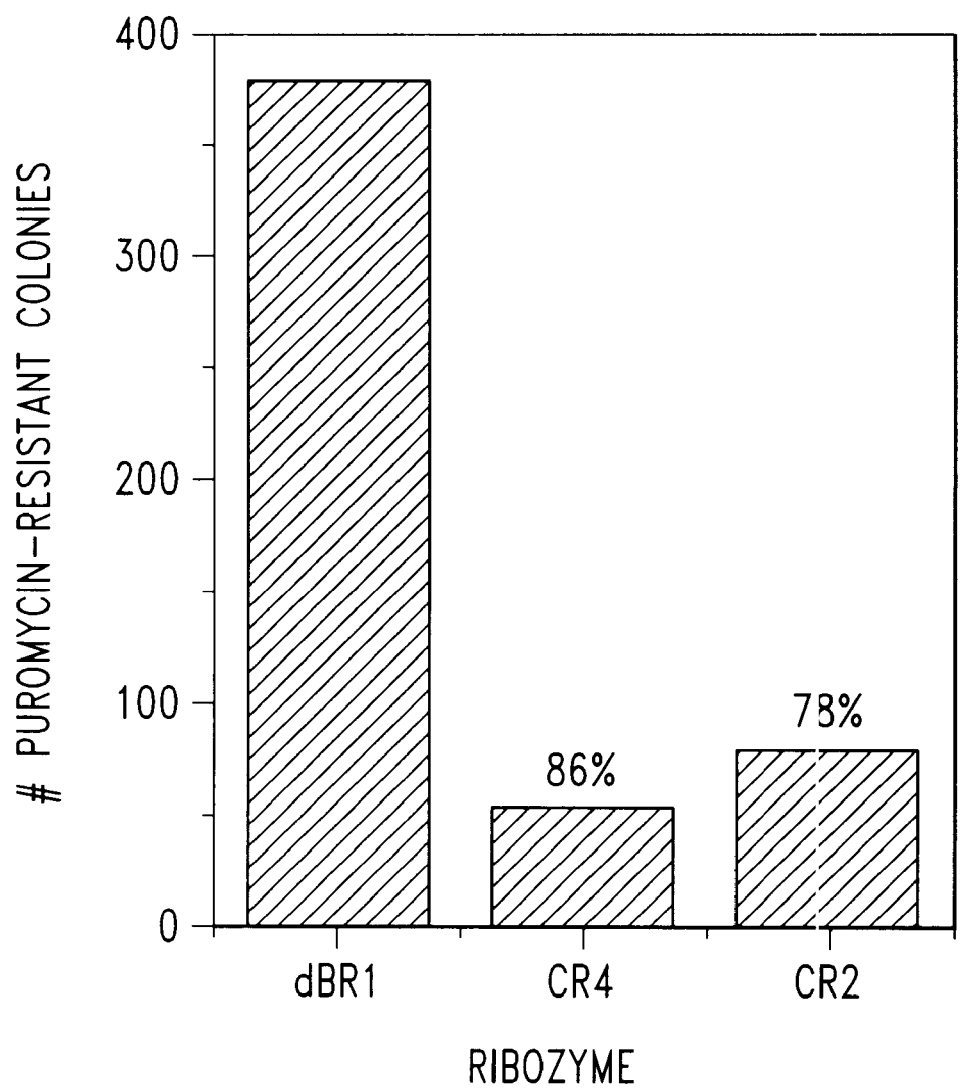
FIGS. 11A, 11B and 11C are three graphs which show ribozyme cleavage obtained in co-transfection experiments.
Figure 11B:
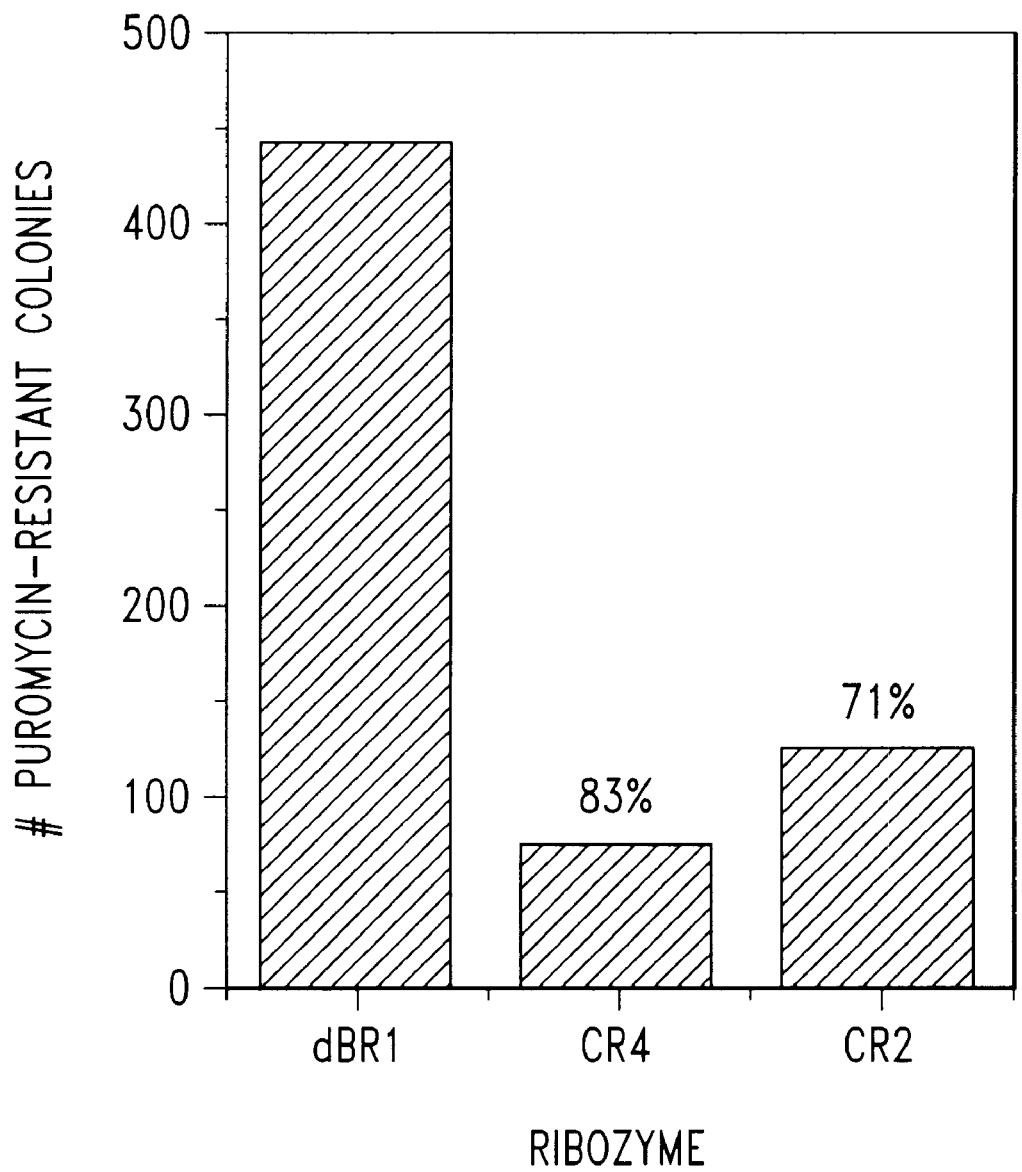

Expression of either Rz CR2 or Rz CR4 results in a 70–90% reduction in puromycin-resistant colonies as compared to the dBR1 negative control (FIG. 11). Results are similar in two human cell lines: HeLa (FIG. 11A) and HT1080 (FIG. 11B). To verify that the ribozymes are exerting their effect via the HCV sequences, similar co-transfections are performed with a pPur plasmid lacking the HCV target sequence. Under these conditions, co-expression of CR2 or CR4 has no effect on the number of puromycin-resistant colonies (data not shown), indicating that the ribozymes are targeting the HCV sequence.

To determine if the activity of CR4 is dose-dependent, co-transfections are performed with varying amounts of pLNT-CR4. DNA molar ratios for the HCV:Rz co-transfections ranged from 1:1 to 1:10, using empty pLNT vector to maintain total DNA at 20 μg. As a negative control, disabled CR4 (dCR4) is also co-transfected at each molar ratio. Again, cells are selected with 1 μg/ml puromycin, starting 24 hours post transfection, and continued for up to two weeks. Puromycin-resistant colonies are visualized by crystal violet staining and counted.

Figure 11C:
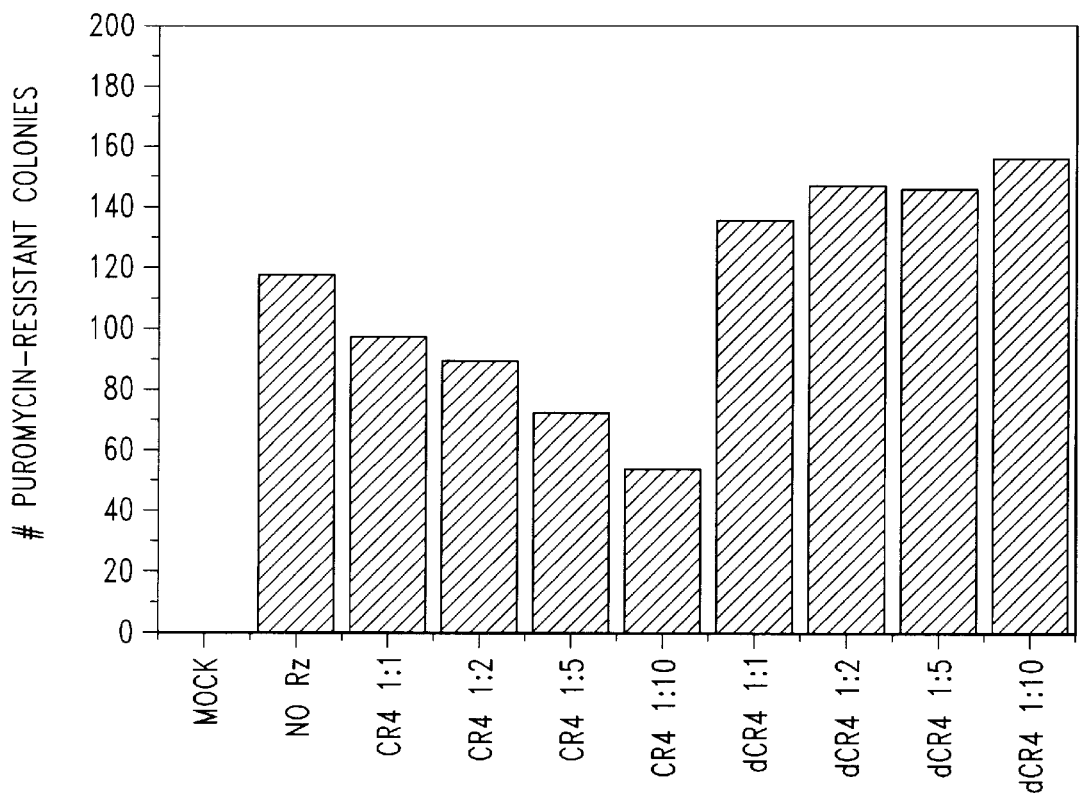

Expression of increasing amounts of CR4, but not dCR4, resulted in a dose-dependent reduction in the number of puromycin-resistant colonies in HT1080 cells (FIG. 11C). Together, the results presented in FIG. 11 indicate that co-expression of the HCV Rz interferes with the expression of the puromycin resistance marker, and appears to exert its effect through cleavage of the HCV target site.

C. Protection Assays

Figure 12:
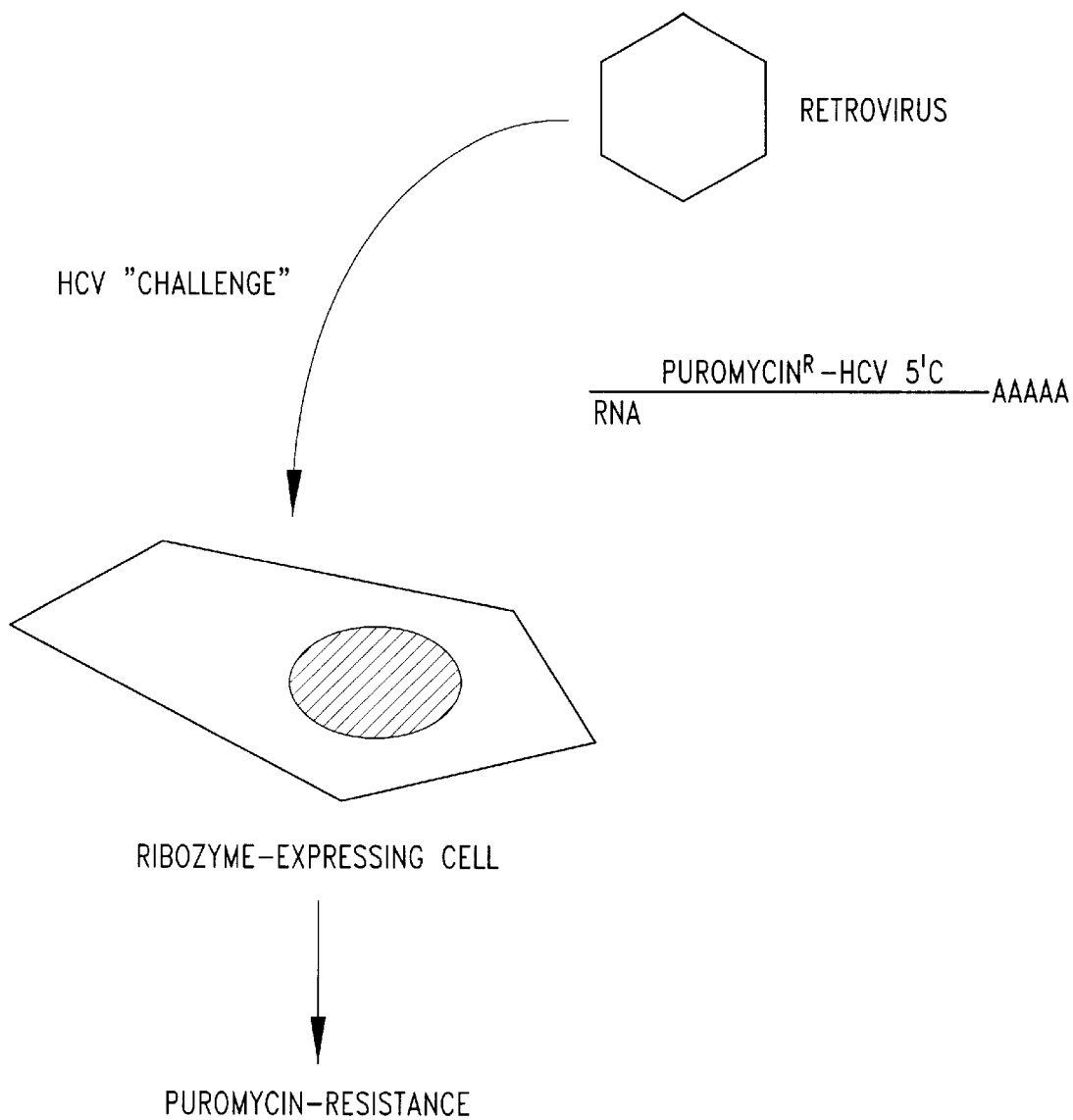
FIG. 12 is a schematic illustration of the experimental design used to test the protective effect of the ribozymes.

Stable expression of HCV Rz's is also tested to determine if it could protect a cell from infection with a related virus that shares some of the properties of HCV. Like HCV, retroviruses also have a positive, single-stranded, RNA genome. Thus, retroviral vector, pLNL-Pur-HCV (FIG. 9D) is constructed to contain an HCV Rz target sequence in tandem with the Puromycin resistance gene. Polyclonal cell lines that stably express each of the ribozymes via the tRNA$^{val}$ promoter are established in the human hepatocellular carcinoma cell line, HepG2, by transduction with retroviral vector, pLNT-Rz (FIG. 2), followed by G418 selection. Helper-free amphotropic retroviral vector is then produced in PA317 cells, using pLNL-Pur-HCV (FIG. 9D), which contains within its (+) strand RNA genome, the HCV 5' UTR and capsid sequences. The HepG2-Rz cell lines are then "challenged" by transduction with the HCV sequence-containing retroviral vector. To determine the level of transduction, cells are selected with 1 μg/ml puromycin starting 24 hours post transduction, and continued for up to two weeks. Puromycin-resistant colonies are stained and counted (see FIG. 12 for a schematic representation of the experiment).

Figure 13:
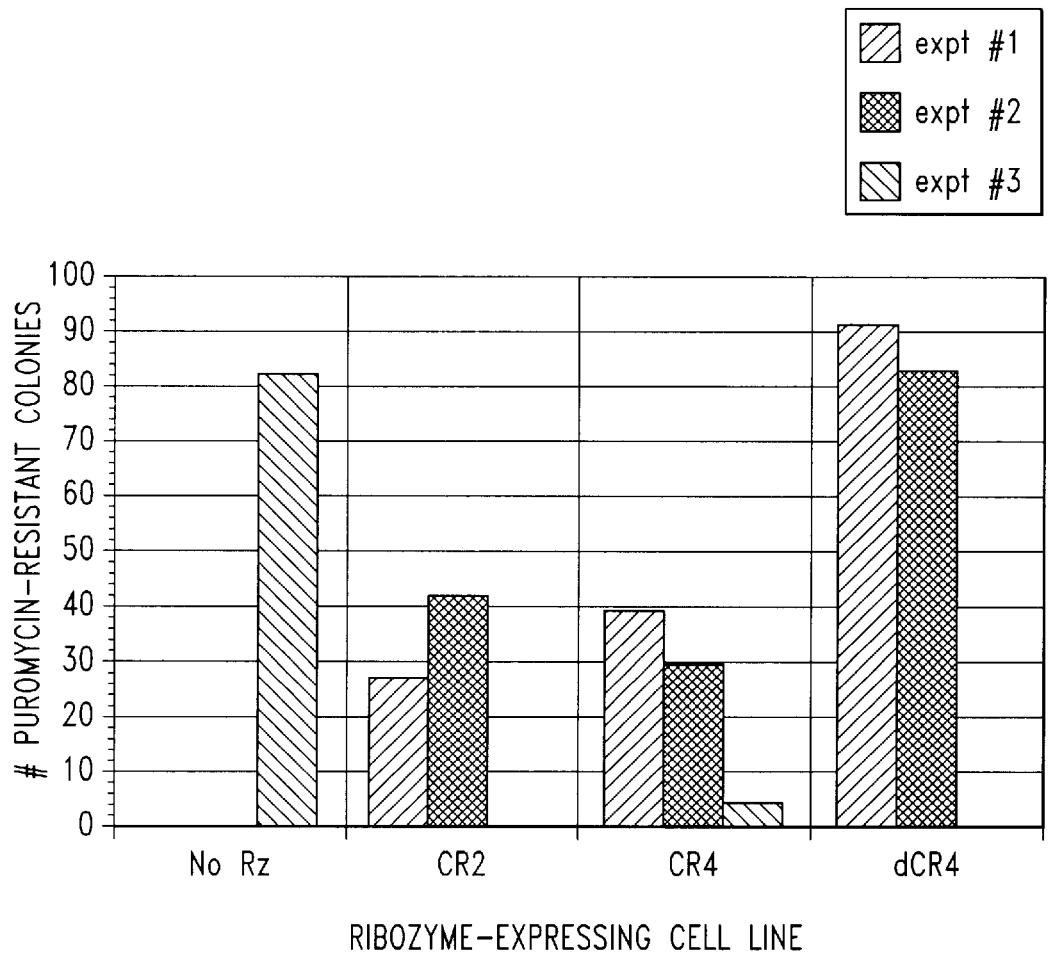
FIG. 13 is a graph showing ribozyme cleavage and subsequent protection of cells from incoming HCV-containing positive-stranded RNA virus.

Stable expression of both the CR2 Rz or the CR4 Rz "protected" the cell from incoming retroviral vector containing HCV Rz target sequences, compared with the disabled Rz control dCR4 (FIG. 13). Similar results are also shown in HeLa cells (data not shown). Together, these results confirm the previous result that the HCV ribozymes could function within human liver cells. Furthermore, these results indicate that stable expression of HCV Rz's can inhibit "infection" with viruses that contain positive-stranded RNA genomes.

Example 6

Testing Additional HCV Ribozyme Target Sites in Tissue Culture

The reporter systems, as described thus far, are suitable only for the analysis of ribozymes targeted to the 5'UTR and capsid regions of HCV. In order to test the additional target sites listed in Table I, in vivo assay systems can be designed which are capable of testing the cleavage by ribozymes of any site within the either the (+) or (−) strand RNA.

A. Analyzing Ribozyme Cleavage in the (+) Strand

Figure 14:
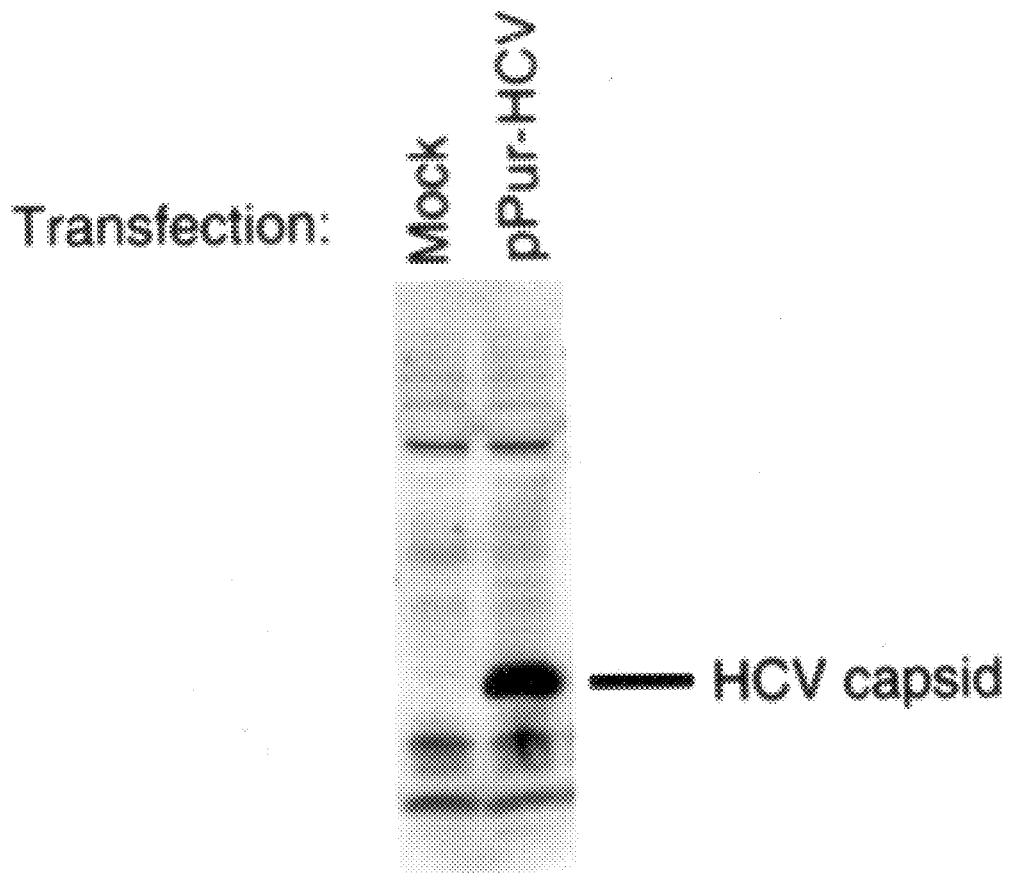
FIG. 14 is a western blot indicating detection of HCV nucleocapsid protein.

The (+) RNA strand of HCV contains the open reading frame responsible for the translation of the 3011 amino acid polyprotein. A western blot assay can be developed, using human antiserum from HCV-infected patients, to detect translation of the nucleocapsid (or capsid) protein in transfected cells (FIG. 14). Briefly, transfection of HT1080 cells with pPur-HCV (see FIG. 9B) results in the transcription of an mRNA containing the HCV 5'UTR and capsid sequences. It has previously been demonstrated the 5'UTR of HCV can act as an Internal Ribosome Entry Site (IRES), which allows protein translation to initiate from within an RNA (Wang et al., *J. Virology* 67:3338–3344, 1993). Thus, the transfected cells translate the capsid sequences and the 21 kD capsid protein is visualized by western blotting (FIG. 14). In this experiment, only the first 1000 nucleotides of HCV are present in the mRNA, resulting in the translation of just the capsid protein. However, when more of the HCV sequence is included (anywhere up to the total 9500 basepairs), a larger polyprotein is translated and the resulting protein detected by our western blot assay is correspondingly larger (not shown). Since the capsid coding region is the first region of the HCV polyprotein to be translated, its detection can be used to visualize translation of any length polyprotein, up to the full size HCV polyprotein of nearly 350 kD. Ribozymes targeted anywhere on the (+) strand RNA would cleave the HCV mRNA, resulting in the translation of a polyprotein smaller than that translated in the absence of ribozyme. This assay can not only detect ribozyme activity, it can also be used to quantitatively compare the activity of various ribozymes targeted to different sites anywhere on the (+) strand.

B. Analyzing Ribozyme Cleavage in the (−) Strand

Figure 15:
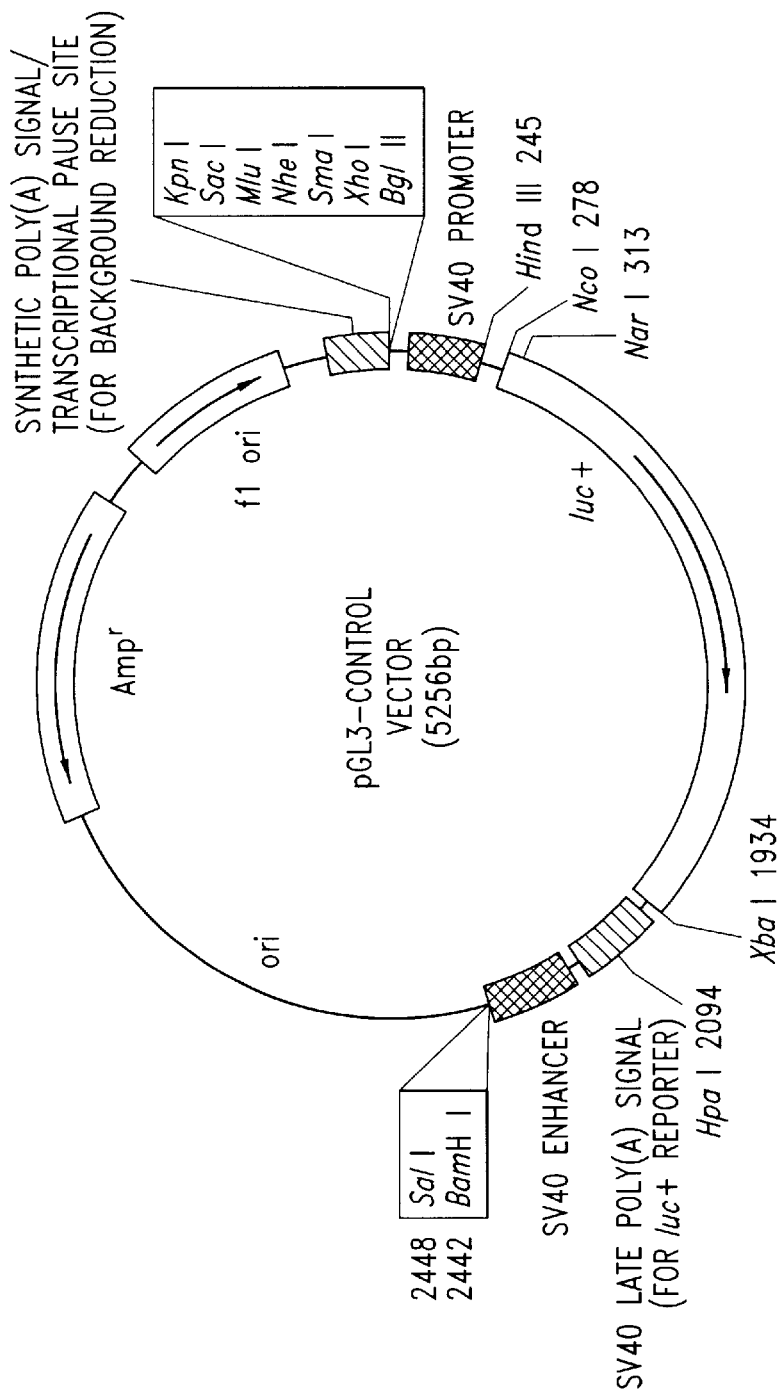
FIG. 15 is a schematic illustration of vector pGL3 (Promega, Madison, Wis.).

Since there is currently no cell culture system that supports HCV replication, and therefore the production of HCV (−) strand RNA, a luciferase reporter system can be developed to analyze the effect of ribozymes targeted against the (−) strand. Briefly, fragments of the (−) strand are cloned into the unique Hind III site upstream of the luciferase coding region in the pGL3 vector (FIG. 15; Promega, Madison, Wis.). These vectors, when transfected into mammalian cells, transcribe mRNA, via the SV40 early promoter, that contains the fragment of the (−) strand RNA upstream of the luciferase coding region. Ribozymes directed against the (−) strand RNA are first cloned into pLNT-Rz (see FIG. 2) and then co-transfected with the HCV-luciferase reporter plasmid. Ribozymes capable of cleaving the (−) strand in vivo will thus result in a decrease in luciferase activity after transfection. Luciferase activity is measured by the Luciferase Assay System (Promega, Madison, Wis.). Similar to the assay system for testing ribozymes on the (+) strand described above, this luciferase-based assay not only can detect ribozyme activity, but can also be used to quantitatively compare the activity of various ribozymes targeted to different sites anywhere on the (−) strand.

Example 7

Construction of Adenovirus and AAV Ribozyme Delivery Vectors

A. Construction and Purification of Adenoviral Delivery Vectors

Figure 16:
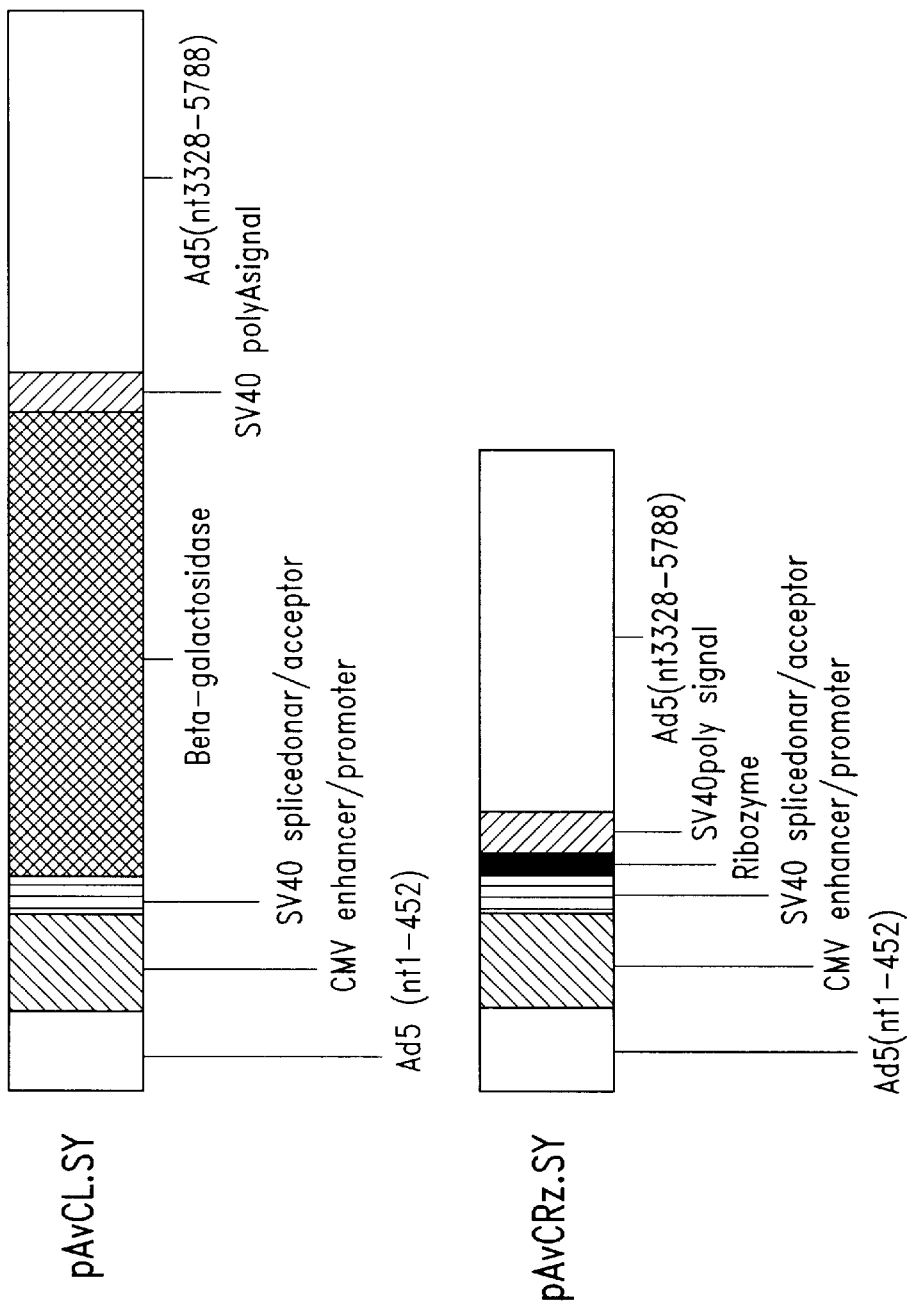
FIG. 16 is a schematic illustration of adenoviral vectors expressing either β-galactosidase or ribozyme.

Recombinant replication-deficient (E1 deletion) adenoviral vectors (Av) containing HCV specific ribozyme genes are constructed by homologous recombination of shuttle plasmid (pAvCRz.SY; FIG. 16) with Ad dl-327 (Jones and Shenk, *Cell* 13:181–188, 1978). Briefly, the shuttle plasmid is a pBR322-based plasmid consisting of the following elements: (1) Ad5 sequence 1–452 (Genebank accession no. M73260; containing the left inverted terminal repeat, encapsidation signals and the E1 a enhancer), artificial XbaI, BamHI and XhoI sites, (2) CMV immediate/early gene promoter and enhancer (from pCMVβ expression vector, Clontech, Palo Alto, Calif.; Boshart et al., *Cell* 41:521–530, 1985), artificial BamHI and XhoI sites, SV40 splice donor/splice acceptor sequence (from pCMVβ expression vector, Clontech, Palo Alto, Calif.), artificial multiple cloning sites include BamHI, NotI, BglII, EcoRI, AscI, NotI, BamHI sites in a contiguous arrangement, SV40 polyadenylation (from pCMVβ expression vector, Clontech, Palo Alto, Calif.), artificial BamHI, SalI and ClaI sites; and (3) an Ad5 sequence used for homologous recombination (Ad5 sequences 3328–5788). HCV-specific ribozyme genes (such as CR2 and CR4 and others) or reporter genes (such as *E coli* β-galactosidase gene from pCMVβ expression vector, Clontech, Palo Alto, Calif.) are cloned into the shuttle plasmid via the multiple cloning site (FIG. 16). Recombinant adenoviral vectors are plaqued and purified from 293 cells co-transfected with both the shuttle plasmid and large ClaI-fragment of dl327. The resulting Av are plaque-purified for at least 2 more times as performed routinely (Yei et al, 1994, *Human Gene Therapy* 5:731–744). Av can be propagated in 293 cells and purified to high titer preparation before use in evaluating the function of anti-HCV Rz.

Figure 17:
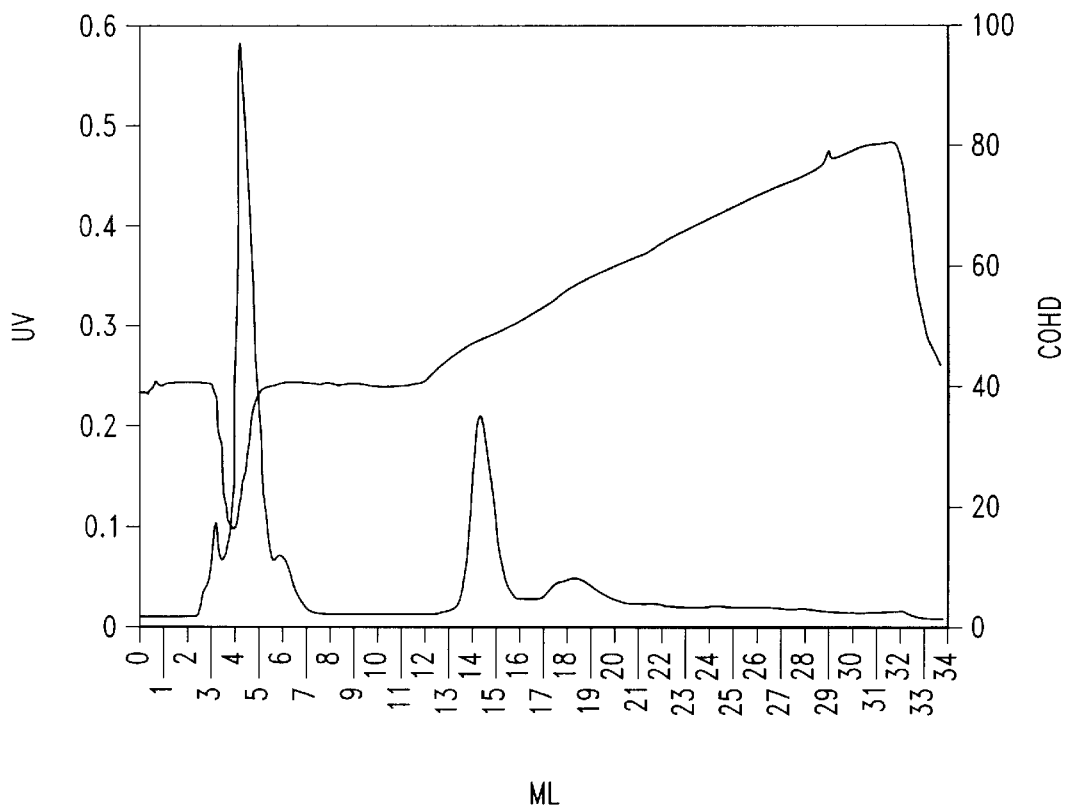
FIG. 17 is a graph which shows FPLC data generated during purification of adenoviral vectors from cell lysates.

Since intravenous use in animals requires the preparation of large amounts of highly purified vector (e.g., Adenoviral vector preparations), within certain embodiments of the invention FPLC may be utilized to purify the relevant viral vector. For example, as shown in FIG. 17, wild-type Adenovirus, used here as a model for Adenoviral vector, can be purified from clarified cell lysates by salt gradient elution of ion-exchange column chromatography. The virus, as measured by an infectivity assay, eluted as a sharp peak at approximately 14–15 ml. It is estimated that the virus is at least 90% pure and results in yields that are comparable to other, less scalable, purification techniques, such as CsCI gradient centrifugation.

B. Construction of AAV Delivery Vectors

Figure 18:
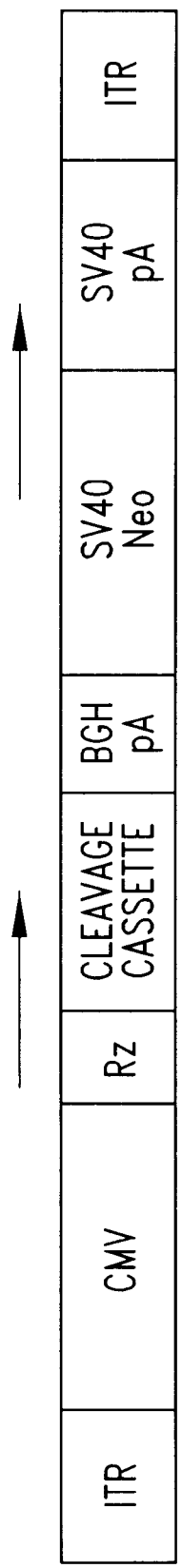
FIG. 18 is a schematic illustration of an AAV ribozyme expression vector.

Recombinant AAV (rAAV) vectors containing HCV specific ribozymes can also be constructed. Potential ribozymes include, but are not limited to CR2 and CR4. Briefly, within preferred embodiments the ribozyme(s) are placed under the control of an CMV promoter, and a selectable marker, such as neomycin resistance, is placed under the control of an SV40 early promoter (FIG. 18). The ribozyme can contain the bovine growth hormone (BGH) polyadenylation signal and can also contain a cleavage cassette which allows for 50% of the ribozyme molecules to be non-polyadenylated. The neo mRNA can be polyadenylated by the SV40 polyadenylation signal. The entire cassette can be flanked by AAV ITRs to allow for packaging into an AAV particle (FIG. 18). To package the AAV vector, poly-1-lysine is crosslinked to the surface of adenovirus type 5 and the positively charged virus is bound to DNAs for rAAV and the AAV helper plasmid pAAV/Ad (pAAV/Ad contains all the necessary AAV complementation functions for packaging of AAV genomes; Samulski et al., *J. Virology* 63:3822–3828, 1989). Subsequently, the adenovirus poly-lysine complex is used to infect HeLa cells and approximately 48 hours post-infection the cells are harvested and lysed by freeze-thaw to release packaged rAAV. The cell lysate is then heated to 56° C. to inactivate replication competent adenovirus and the rAAV is then purified or used crude to titer and transduce liver cells.

Example 8

In Vitro Cleavage of HCV Negative Genomic Strand RNA by Ribozymes

Ribozyme genes which encode target HCV (−) strand RNA were synthesized and cloned into in vitro transcription vectors (pGEM-7Z, Promega, Madison, Wis.) as described in Example 2. The resultant plasmids, designated as pGem7Z-(−) ribozyme, were linearized with NsiI (immediately downstream of the cloned gene) and transcribed in vitro by T7 (Welch et al., *Gene Therapy* 3:994–1001, 1996). The reactions were treated with RQ 1 DNase, according to information provided by the manufacturer (Promega) and the transcripts were gel purified.

HCV negative strand RNA substrates were also obtained by in vitro transcription, using the plasmid pGEM7-HCV5' for long substrate synthesis (471 bp in length). The short substrate was made by annealing 2 oligos: one with cleavage site and one with T7 promoter, and filled in with T4 DNA polymerase as described previously (Welch et al., 1996, supra)

Figure 19:
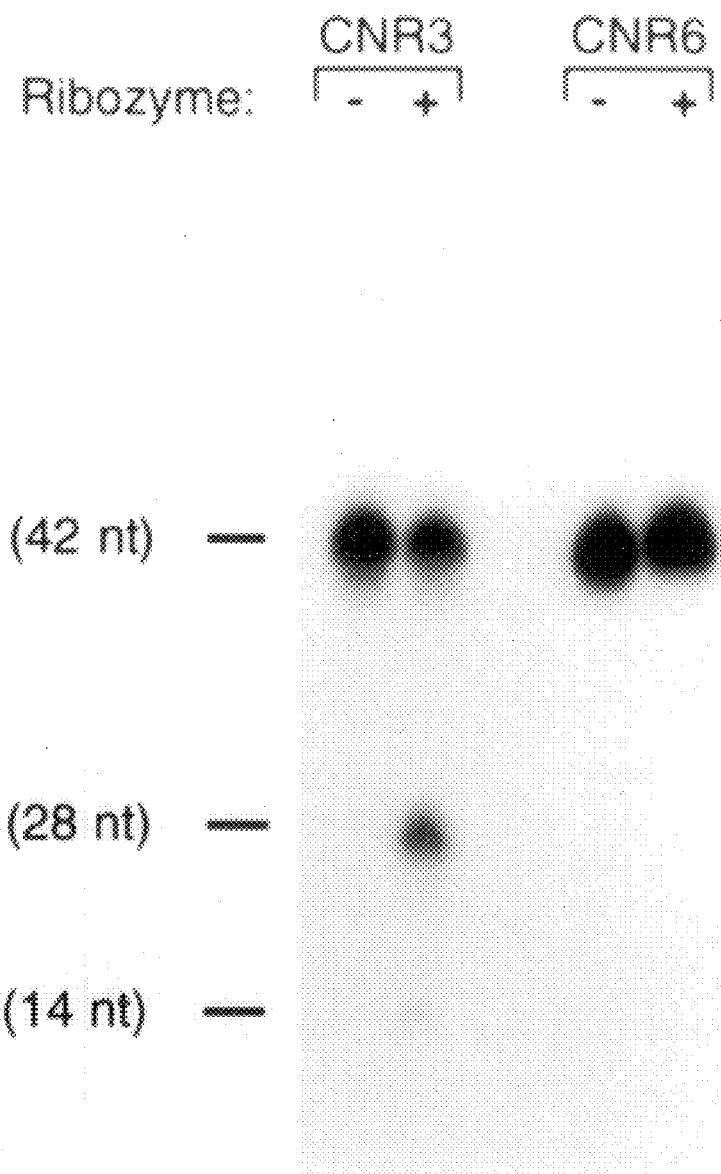
FIG. 19 is an autorad which shows the results of in vitro cleavage of short (<50 nucleotides) substrates by two ribozymes (CNR3 and CNR6) against the (−) strand of HCV.
Figure 20:
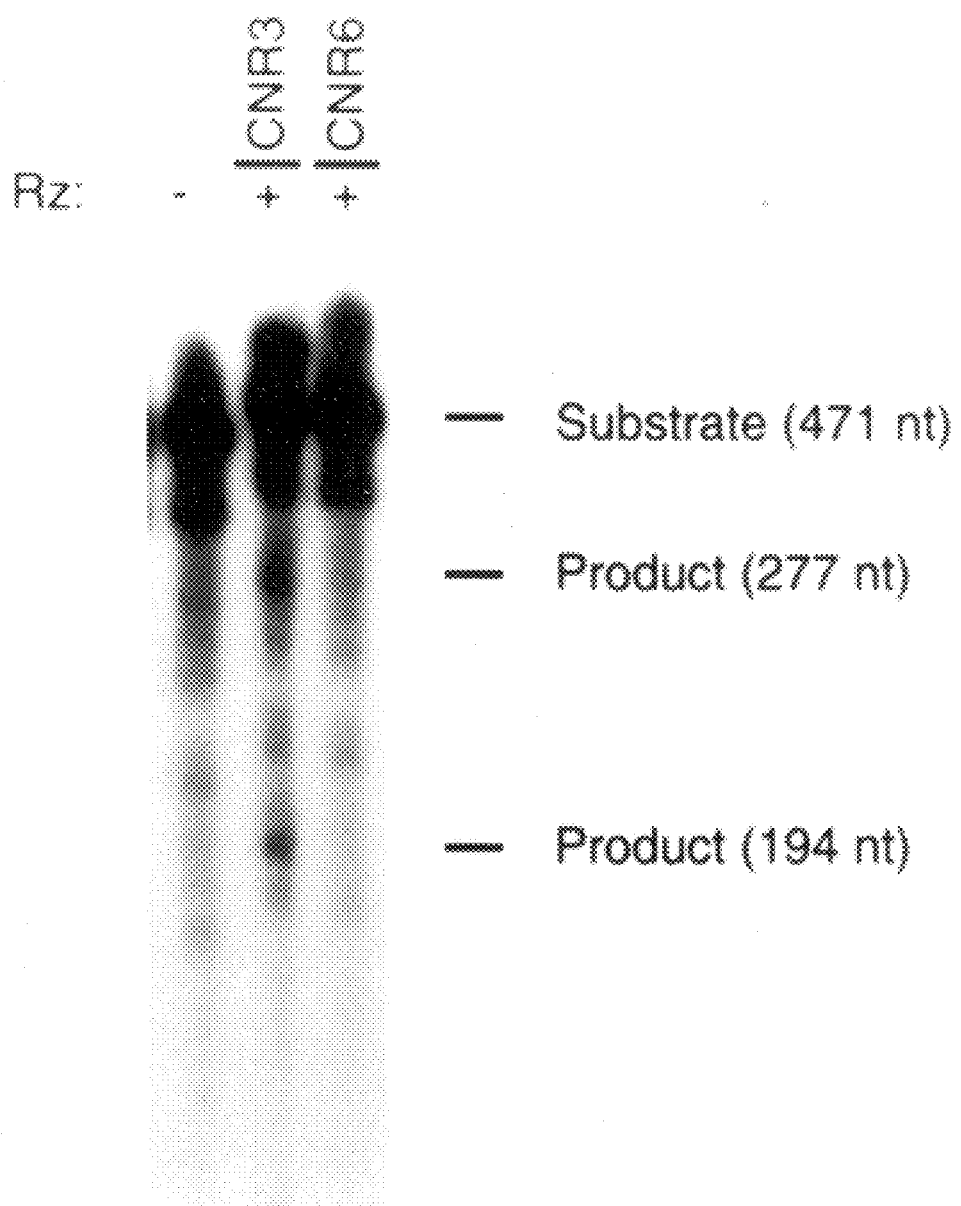
FIG. 20 is an autorad which shows the results of in vitro cleavage of long substrates by two ribozymes (CNR3 and CNR6) against the (−) strand of HCV.

In vitro cleavage assays were performed essentially as described above. Results are shown in FIGS. 19 and 20. Briefly, the blots in FIGS. 19 and 20 clearly indicate that the CNR3 Rz cleaves the short (19) and long (20) negative strand HCV RNA substrate.

Example 9

Figure 21:
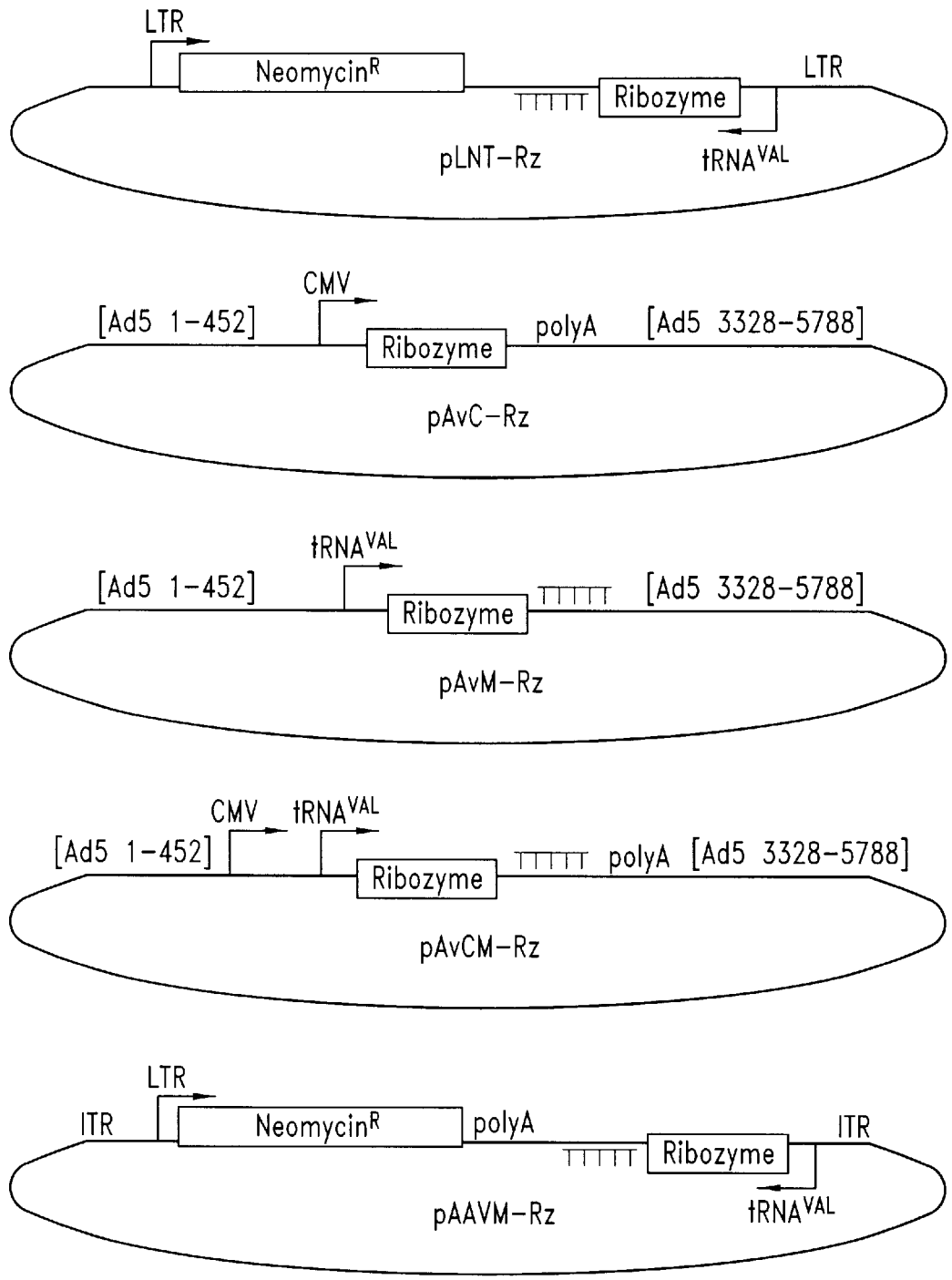
FIG. 21 is a schematic illustration of vectors pLNT-Rz, pAvC-Rz, pAvM-Rz, pAvCM-Rz and pAAVM-Rz.

Construction of Adenovirus and AAV Ribozyme Delivery Vectors With Various Promoters A. Construction of Adenoviral Vectors Replication-deficient adenoviral vectors expressing the catalytically active Rz (CR4) identified in Example 5 driven by various promoter were constructed essentially as described in Example 7, in order to contain a tRNA$^{val}$ promoter (Yu et al., *PNAS* 84:1005, 1993) or CMV promoter or both. The resulting plasmids are illustrated in FIG. 21: pAvC-Rz express Rz under CMV promoter, pAvM-Rz express Rz under control of tRNA$^{val}$ promoter and pAvCM-Rz express Rz from both CMV and tRNA$^{val}$ promoters.

B. Construction of AAV Vectors

Figure 22:
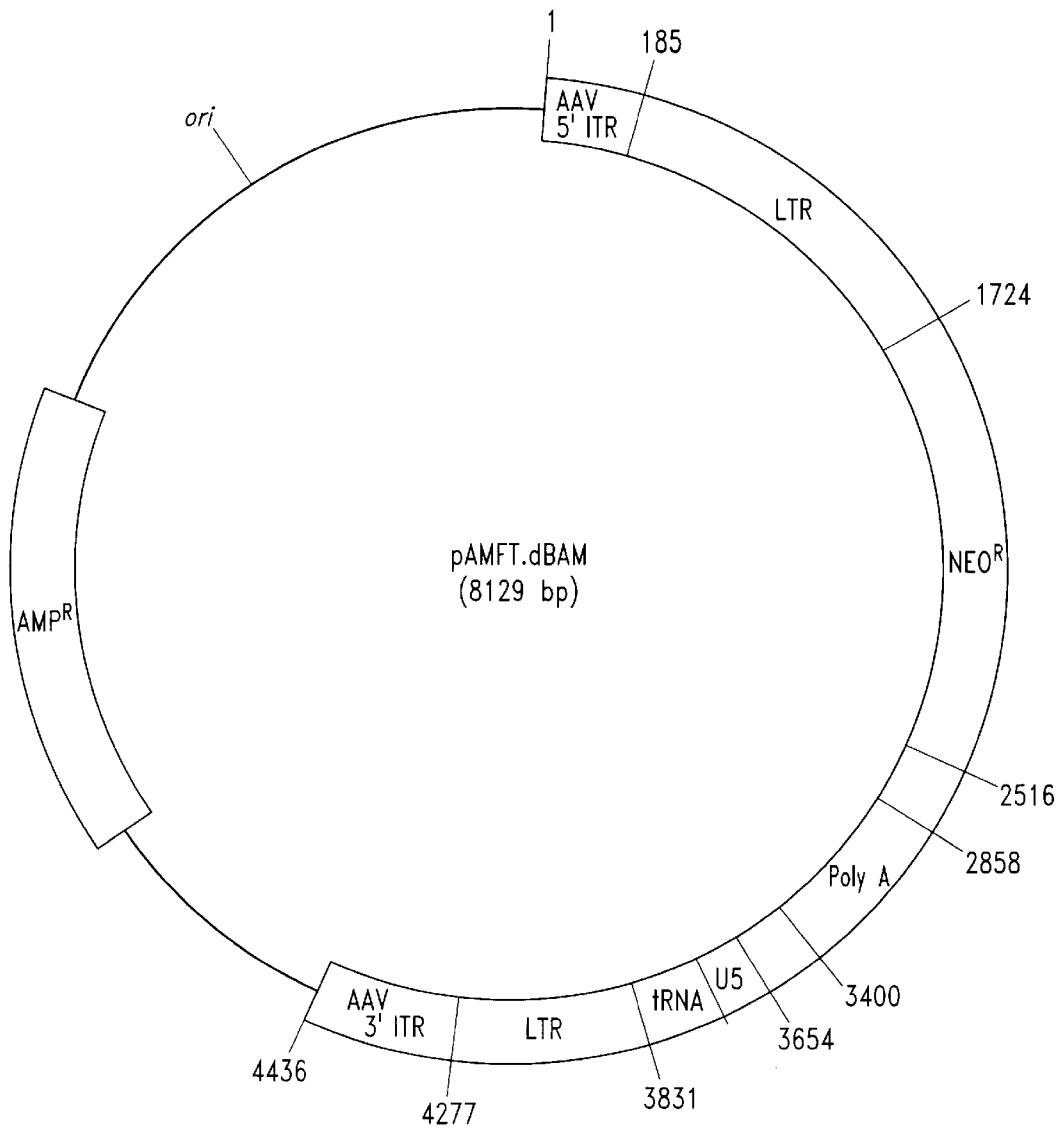
FIG. 22 is a schematic illustration of pAMFT.dBAM.

The CR4 Rz gene was also cloned into pAMFT.dBam plasmid to generate rAVV vectors expressing CR4 from tRNA$^{val}$ promoter. Briefly, pAMFT.dBam (FIG. 22) is a recombinant plasmid carrying 1) 5' and 3' inverted terminal repeats (ITR) of adeno-associated viral genome; 2) cassette for transcription of Rz gene via tRNA$^{val}$ promoter; 3) neomycin resistance marker driven by MMLV LTR. The resultant plasmid for generating AAV vectors that express CR4 ribozyme under control of tRNA$^{val}$ promoter is designated as pAAVM-CR4 (FIG. 21).

Example 10

Effect of CR4 Rz in Reducing HCV Gene Expression

Figure 23:
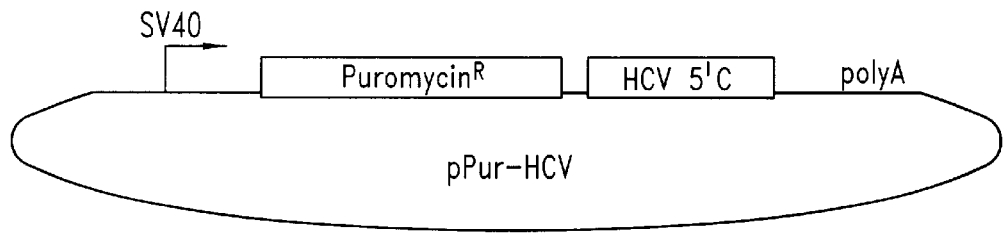
FIG. 23 is a schematic illustration of vectors pPur-HCV, pLNL-PUR-HCV and pGem4-HCV 5'C.
Figure 23:
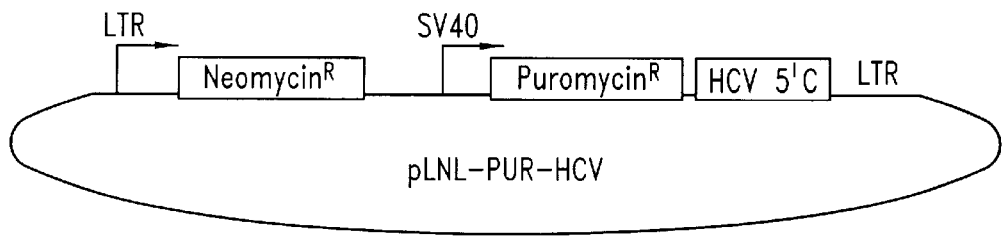
Figure 23:
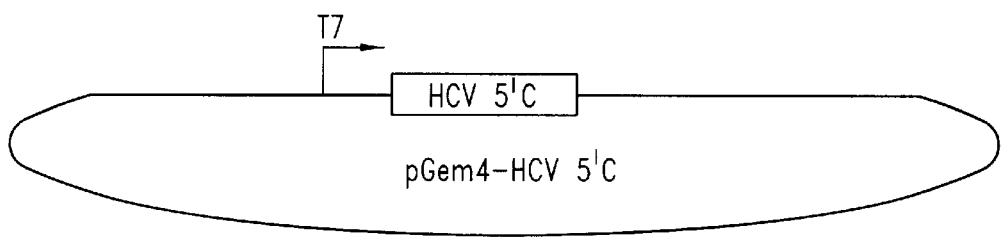

CR4 Rz activity in reducing HCV gene expression was tested in tissue culture. Briefly, CR4 Ribozyme was expressed from pAvC-CR4 described in Example 9. Western blot to detect HCV core antigen was used to evaluate the effectiveness of ribozyme in inhibiting the intracellular synthesis of HCV capsid in tissue culture. In particular, HT1080 cells were co-transfected by pPur-HCV (see FIG. 23) and pAvC-CR4 at a molar ratio of 1:10 of 1:20 using method described in Example 5. Ribozymes tested included CR4 and disabled CR4 (dCR4). Cells were harvested at 24 hours post transfection and processed for HCV core Western blot.

Figure 24:
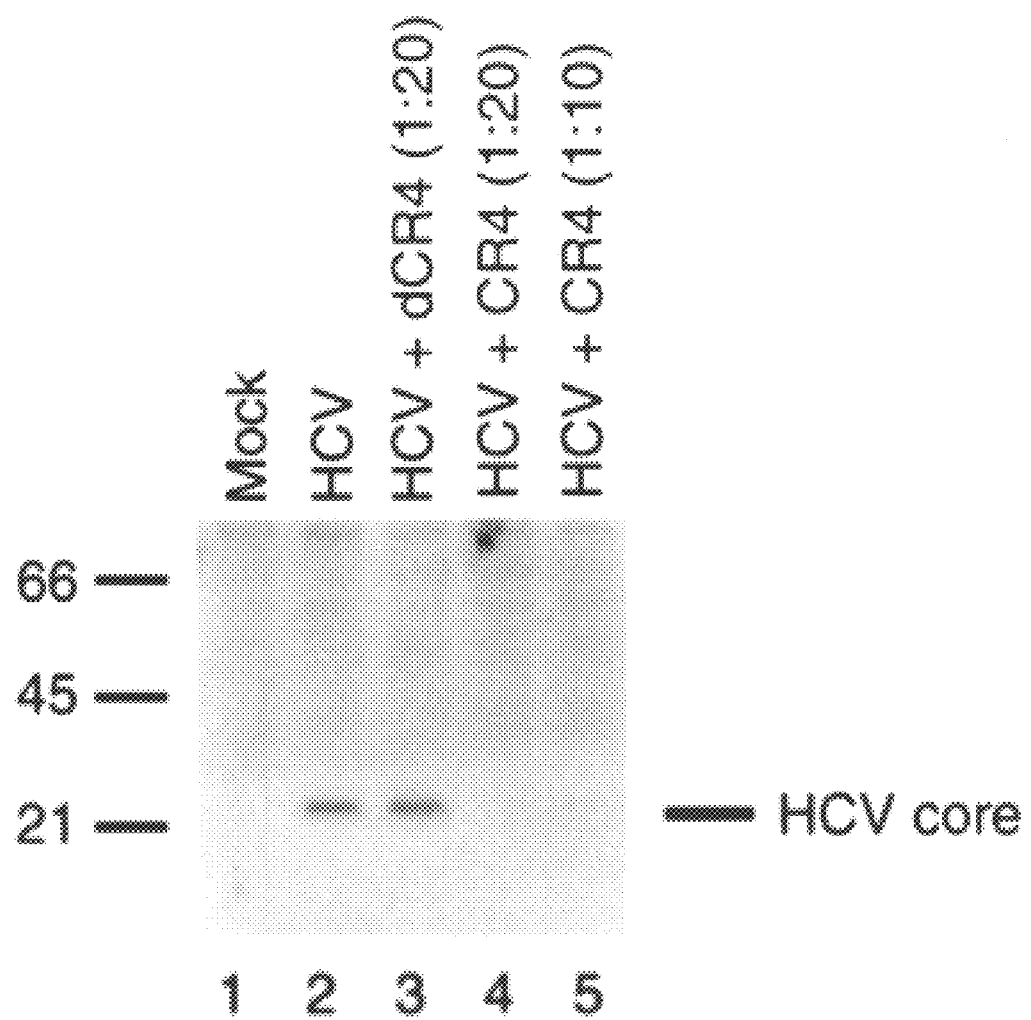
FIG. 24 is a western blot which shows expression of HCV core protein following transfection into HT1080 cells.

As shown in FIG. 24, co-transfection of pAvC-CR4 at the molar ratios tested (1:10 and 1:20) results in nearly complete shut off of HCV core expression while disabled form of CR4 (dCR4) had no effect (FIG. 24).

Example 11

Figure 25A:
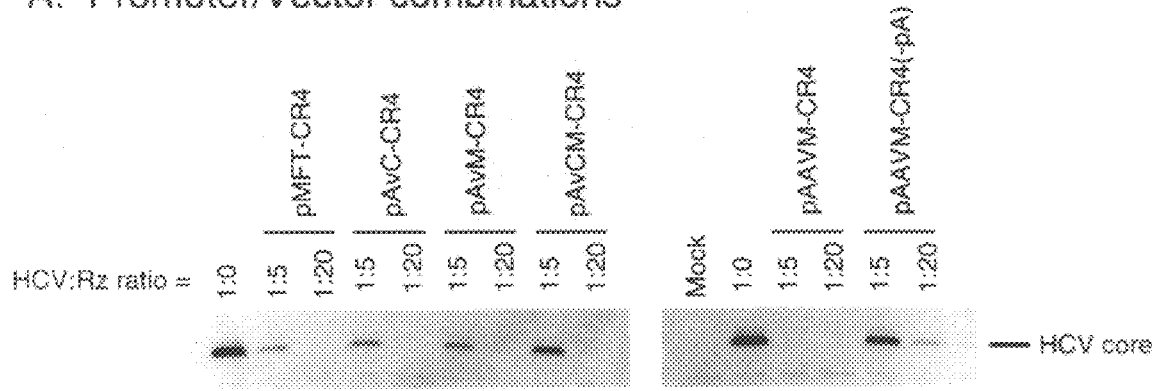
FIG. 25A is a blot which shows the ability of different promoter/vector combinations to reduce viral core expression in cell culture. pAAVM-CR4 shows the greatest efficacy.
Figure 25B:
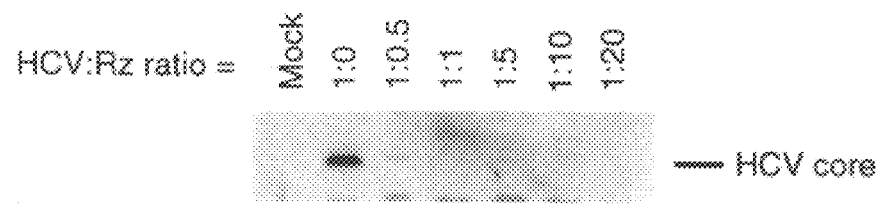
FIG. 25B is a blot which shows the further titration of pAAVM-CR4 and its effect on viral core expression.

Effect of Different Promoter/Vector Combinations in Reducing HCV Gene Expression Effect of different promoter/vector combination on CR4 Rz activity in reducing HCV gene expression was further tested in tissue culture. Briefly, the studies were done in a way similar to that described in Example 10, except that CR4 Rz was expressed from different promoter/vector constructs. Expression of CR4 from different constructs all resulted in reduced HCV core expression (FIG. 25, panel A), as seen in Example 10. However, pAAVM-CR4 (adeno-associated virus DNA backbone with tRNA$^{val}$ pol III promoter expressing CR4 Rz) shows the greatest efficacy (FIG. 25-A).

The activity of pAAVM-CR4 was also titered for reducing viral core expression by co-transfected the cells with HCV:Rz ratio at 1:0, 1:0.5, 1:1, 1:5, 1:10 and 1:20. Complete inhibition of core protein expression even at 1:1 ratio. Significant reduction seen at 1:0.5 ratio (FIG. 25, panel B).

Example 12

In Vivo Expression of Rz CR4 in Liver Cells

The ability of recombinant adenovirus to deliver and express a ribozyme gene in human liver cells was evaluated essentially as follows. Briefly, adenovirus was generated that carries the CR4 gene driven by the CMV promoter (AvC-CR4). Human hepatoma cells (Huh7) were transduced with vector at m.o.i. of 0, 1, 5, 10 or 50 and cellular RNA was harvested at 1 or 3 days post transduction.

Figure 26:
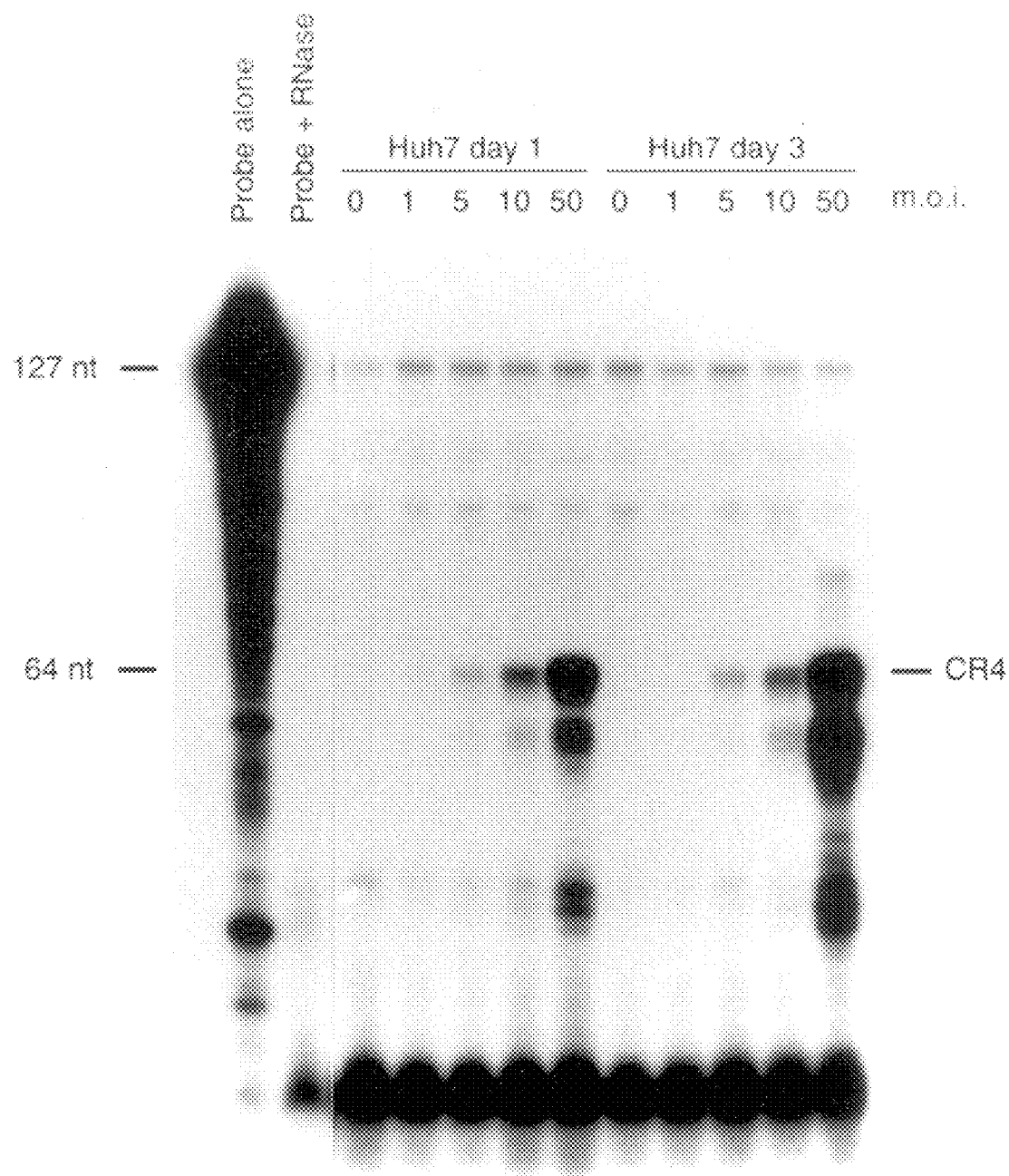
FIG. 26 shows the results of an RNase protection assay performed to measure expression of ribozyme CR4 in human liver cells.

RNase protection assay (Promega, Madison, Wis.) was then performed in order to measure the expression of ribozyme. Briefly, as shown in FIG. 26, CR4 ribozyme was expressed equally at day 1 and day 3 post transduction and expression levels indicated a dose-response dependent on the amount of virus transduced. These results indicate that adenovirus can be used to deliver and direct expression of a ribozyme gene in human liver cells.

Example 13

Infectivity of Primary Normal Human Hepatocytes With Either Adenoviral or Adeno-associated Viral Vector The infectivity of primary normal human hepatocytes to the AV and AAV vector constructs were tested essentially as described below. Briefly, primary normal human hepatocytes were infected with either AV or AAV vector that carrying beta-galactosidase gene at various MOI. At 24 hours post infection, cells were processed for lacZ staining.

Number of cells stained blue due to transduction of the vectors were counted.

Figure 27:
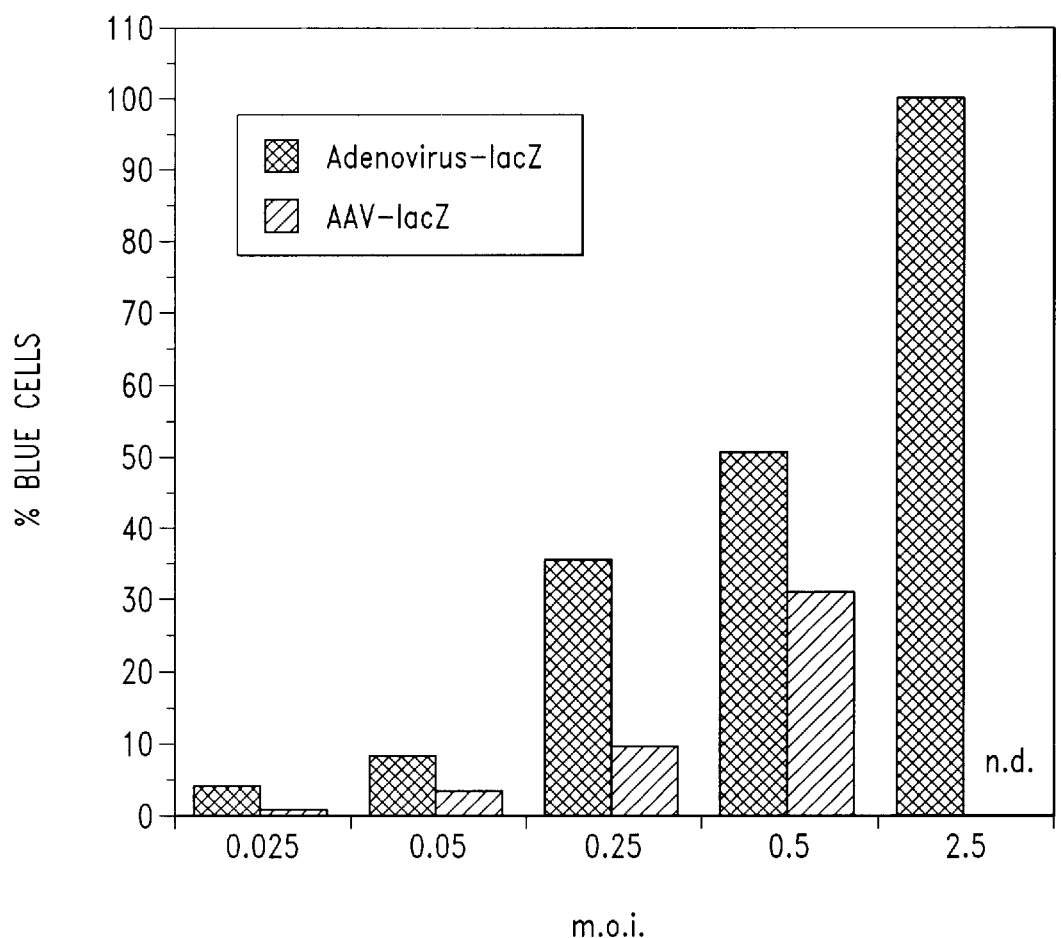
FIG. 27 is a table which compares the infectivity of primary normal human hepatocytes with either recombinant adenovirus or recombinant adeno-associated virus carrying the β-galactosidase gene.

Results are shown in FIG. 27. Briefly, both AV and AAV can efficiently infect and transduce the primary hepatocytes in culture with 100% infectivity.

Example 14

HCV Core Reduction by Adenovirus- or AAV-delivered CR4 Gene

The anti-HCV efficacy of the CR4 gene as delivered by adenovirus or AAV was also assessed utilizing the following protocol. Briefly, human HT1080 cells were transduced with either adenovirus-CR4 or AAV-CR4 (m.o.i.=5 for both) where the ribozyme gene is under the control of the human tRNA$^{val}$ promoter. As controls, adenovirus-NULL (no ribozyme expressed) or AAV-MFT (irrelevant ribozyme against HIV) were transduced under the same conditions. Cells were grown for 24 hours post transduction, at which point they were challenged with our surrogate HCV infection system wherein the HCV target sequences are engineered into the positive RNA strand of a retrovirus (LNL-PUR-HCV, see Example 5). Twenty-four hours after challenge, cell lysates were analyzed by anti-HCV core western blotting (upper panels).

Figure 28A:
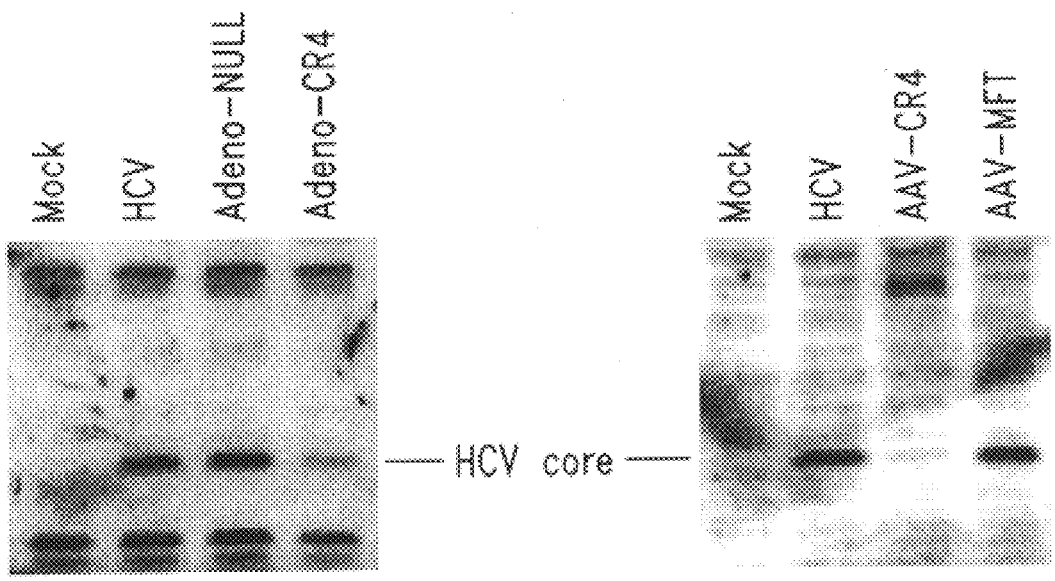
FIG. 28A is a Western blot which depicts HCV core reduction by adenovirus- or AAV-delivered CR4 gene.
Figure 28B:
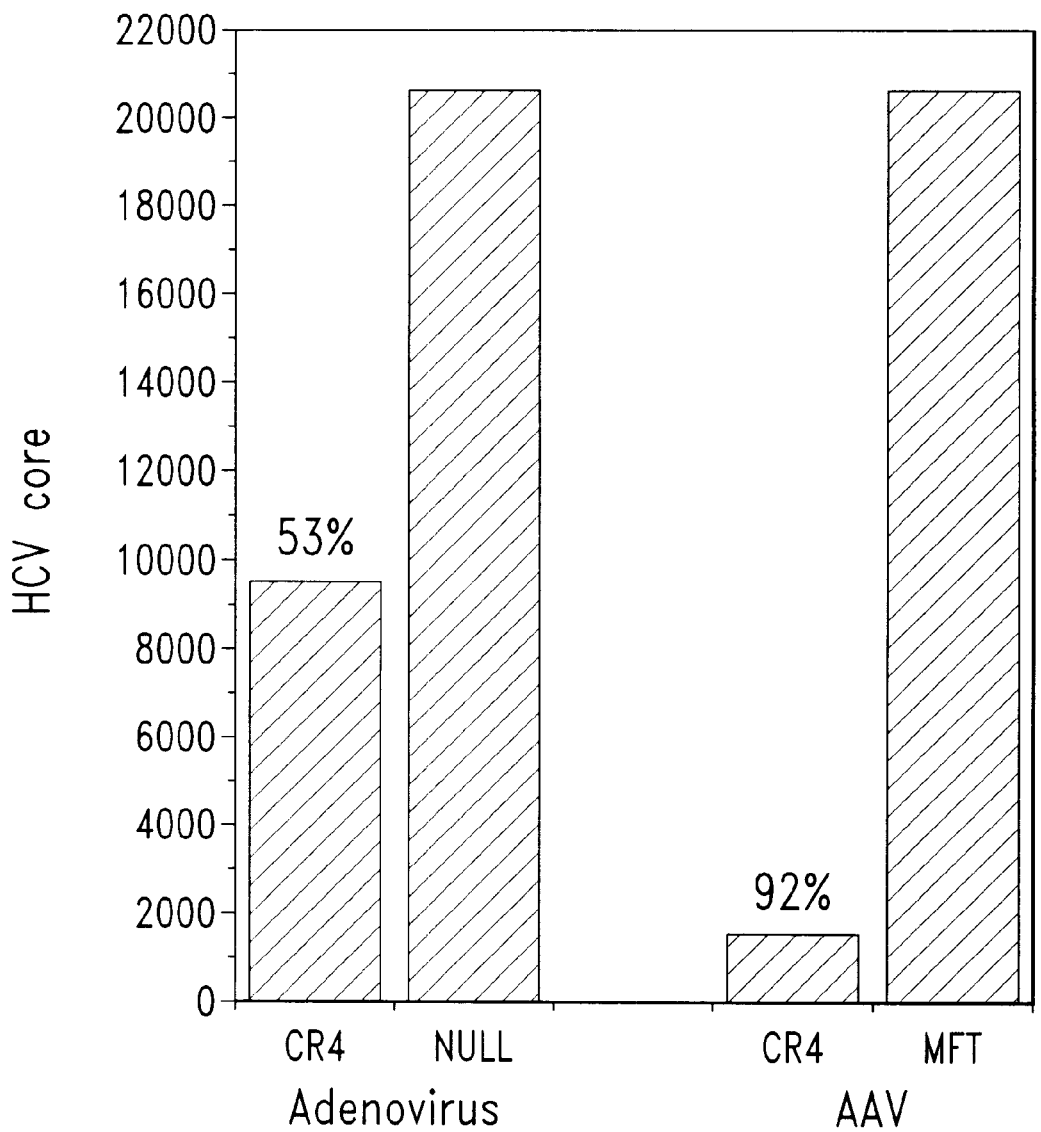
FIG. 28B is a graph which provides a quantitative analysis of the Western blot in FIG. 28A.

Results are shown in FIGS. 28A and 28B. Briefly, CR4 efficiently inhibited HCV core expression when delivered by either adenovirus or AAV, relative to the controls listed above or to the control of no ribozyme gene delivered ("HCV" lanes). The lower panel (FIG. 28B) is a quantitative analysis of the western blot, and the percent reduction relative to the NULL or MFT control is indicated. This data indicates that the CR4 ribozyme gene can be delivered by either adenovirus or AAV to yield an effective anti-HCV drug.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A ribozyme having the ability to inhibit replication, infectivity, or gene expression of a hepatitis C virus wherein the ribozyme is directed to a target sequence selected from the group consisting of SEQ. ID NO. 38, 39, 40, 41, 42, 43 44, 54, and 65.

2. The ribozyme according to claim 1 wherein said ribozyme is a hairpin ribozyme.

3. A nucleic acid molecule encoding a ribozyme according to claims 1 or 2.

4. The nucleic acid molecule of claim 3 wherein the nucleic acid molecule is DNA.

5. A host cell containing the ribozyme or nucleic acid molecule according to any one of claims 1 or 2.

6. A vector, comprising a promoter operably linked to the nucleic acid molecule according to claim 3.

7. The vector according to claim 6, wherein said promoter is a polIII or CMV promoter.

8. The vector according to claim 6 wherein said vector is a plasmid, a viral vector, retrotransposon or a cosmid.

9. The vector according to claim 6 wherein said viral vector is a recombinant adenoviral or retroviral vector.

10. A host cell containing the vector according to claim 6.

11. A method for producing a ribozyme, the ribozyme being able to inhibit hepatitis C viral infection, replication, or gene expression in a cell, comprising providing DNA encoding a ribozyme according to any one of claims 1 to 2 under the transcriptional control of a promoter, and transcribing the DNA to produce said ribozyme.

12. The method according to claim 11, further comprising the step of purifying the ribozyme.

13. The method according to claim 11 wherein said ribozyme is produced in vitro.

14. The method according to claim 11 wherein said ribozyme is produced in vivo in a cell culture.

15. A method of interfering with hepatitis C virus (HCV) replication or gene expression in a cell infected in a cell culture with HCV, which comprises introducing into the cell an effective amount of the ribozyme according to claims 1 or 2.

16. A vector, comprising a promoter operably linked to the nucleic acid molecule according to claim 4.

17. A method of interfering with hepatitis C virus (HCV) replication or gene expression in a cell infected in a cell culture with HCV, which comprises introducing into the cell an effective amount of a vector according to claims 7 or 16.

18. The method according to claim 15, wherein said cell is a human cell.

19. The method according to claim 17 wherein said vector is a recombinant adenoviral or retroviral vector.

20. A composition, comprising a ribozyme according to claims 1 or 2, in combination with a pharmaceutically acceptable carrier or diluent.

21. A composition, comprising a nucleic acid molecule according to claim 3, in combination with a pharmaceutically acceptable carrier or diluent.

22. A composition, comprising a vector according to any one of claims 6 to 9, in combination with a pharmaceutically acceptable carrier or diluent.

23. A host cell containing the ribozyme or nucleic acid molecule according to claim 3.

24. The method according to claim 14 wherein said cell is a human cell.

25. A composition, comprising a nucleic acid molecule according to claim 4, in combination with a pharmaceutically acceptable carrier or diluent.

26. The vector according to claim 16 wherein said promoter is a polIII or CMV promoter.

27. The vector according to claim 16 wherein said vector is a plasmid, a viral vector, retrotransposon or a cosmid.

28. The vector according to claim 16 wherein said viral vector is a recombinant, adenoviral or retroviral vector.

29. A host cell containing the vector according to claim 16.

* * * * *

UNITED STATES PATENT AND TRADEMARK OFFICE
CERTIFICATE OF CORRECTION

PATENT NO.    : 6,043,077
DATED         : March 28, 2000
INVENTOR(S)   : Jack R. Barber, et al.

Page 1 of 1

It is certified that error appears in the above-identified patent and that said Letters Patent is hereby corrected as shown below:

Related U.S. Application Data,
Lines 1-3, "Continuation-in-part of application No. 08/608,862, filed as application No. PCT/US97/03304, Feb. 27, 1997, abandoned." should read -- Continuation-in-part of application No. 08/608,862, Feb. 29, 1996, and claims priority from PCT/US97/03304, Feb. 27, 1997, abandoned. --.

Claim 17, Column 48,
Line 50, "claims 7 or 16" should read -- claims 6 or 16 --.

Claim 28, Column 50,
Line 4, "recombinant, adenoviral" should read -- recombinant adenoviral --.

Signed and Sealed this

Eleventh Day of September, 2001

*Attest:*

*Nicholas P. Godici*

NICHOLAS P. GODICI
*Attesting Officer*    *Acting Director of the United States Patent and Trademark Office*